United States Patent
Nakajima et al.

(10) Patent No.: US 11,363,961 B2
(45) Date of Patent: Jun. 21, 2022

(54) BIOLOGICAL INFORMATION ANALYSIS DEVICE, SYSTEM, AND PROGRAM

(71) Applicants: Omron Corporation, Kyoto (JP); OMRON HEALTHCARE Co., Ltd., Kyoto (JP)

(72) Inventors: Hiroshi Nakajima, Kyoto (JP); Hirotaka Wada, Kyoto (JP); Naoki Tsuchiya, Otsu (JP); Masaaki Kasai, Nara (JP); Eriko Kan, Kyoto (JP); Toru Uenoyama, Kyoto (JP); Keiichi Obayashi, Tokyo (JP); Ayako Kokubo, Uji (JP); Yuya Ota, Kyoto (JP); Toshikazu Shiga, Otsu (JP); Mitsuo Kuwabara, Hirakata (JP); Hironori Sato, Moriyama (JP); Ken Miyagawa, Kyoto (JP); Masakazu Tsutsumi, Muko (JP)

(73) Assignees: Omron Corporation, Kyoto (JP); OMRON HEALTHCARE Co., Ltd., Kyoto (JP)

( * ) Notice: Subject to any disclaimer, the term of this patent is extended or adjusted under 35 U.S.C. 154(b) by 0 days.

(21) Appl. No.: 16/092,151

(22) PCT Filed: Apr. 14, 2017

(86) PCT No.: PCT/JP2017/015281
§ 371 (c)(1),
(2) Date: Oct. 8, 2018

(87) PCT Pub. No.: WO2017/179700
PCT Pub. Date: Oct. 19, 2017

(65) Prior Publication Data
US 2019/0175027 A1   Jun. 13, 2019

(30) Foreign Application Priority Data
Apr. 15, 2016 (JP) .............................. JP2016-082463

(51) Int. Cl.
*A61B 5/029* (2006.01)
*A61B 5/08* (2006.01)
(Continued)

(52) U.S. Cl.
CPC ............ *A61B 5/029* (2013.01); *A61B 5/0002* (2013.01); *A61B 5/021* (2013.01); *A61B 5/022* (2013.01);
(Continued)

(58) Field of Classification Search
CPC .................................................. A61B 5/02108
See application file for complete search history.

(56) References Cited

U.S. PATENT DOCUMENTS

| | | | |
|---|---|---|---|
| 4,365,636 A | 12/1982 | Barker | |
| 5,400,793 A * | 3/1995 | Wesseling | A61B 5/029 600/485 |

(Continued)

FOREIGN PATENT DOCUMENTS

| | | |
|---|---|---|
| CN | 1140582 A | 1/1997 |
| CN | 1158077 A | 8/1997 |

(Continued)

OTHER PUBLICATIONS

International Search Report issued in Application No. PCT/JP2017/015274, dated Jun. 20, 2017 (2 pages).
(Continued)

*Primary Examiner* — Rex R Holmes
*Assistant Examiner* — Jennifer L Ghand
(74) *Attorney, Agent, or Firm* — Osha Bergman Watanabe & Burton LLP

(57) ABSTRACT

A biological information analysis device including: an indicator extraction unit configured to extract an indicator indicating a cardiac state, from data regarding blood pressure waveforms that are consecutively measured by a sensor
(Continued)

that is configured to be worn on a body part of a user and to be capable of non-invasively measuring a blood pressure waveform for each heartbeat; and a processing unit configured to output the indicator extracted by the indicator extraction unit. The indicator extraction unit is configured to extract a value of a cardiac load indicator for each heartbeat, from the data regarding blood pressure waveforms, and calculate the indicator indicating the cardiac state, based on characteristics related to distribution of values of the cardiac load indicator corresponding to a plurality of heartbeats.

8 Claims, 8 Drawing Sheets

(51) Int. Cl.
| | | |
|---|---|---|
| A61B 5/024 | (2006.01) | |
| A61B 5/316 | (2021.01) | |
| A61B 5/352 | (2021.01) | |
| A61B 5/022 | (2006.01) | |
| A61B 5/0205 | (2006.01) | |
| A61B 5/021 | (2006.01) | |
| A61B 5/00 | (2006.01) | |
| G16H 10/40 | (2018.01) | |
| G16H 50/20 | (2018.01) | |
| A61B 5/02 | (2006.01) | |
| A61B 5/11 | (2006.01) | |
| A61M 16/00 | (2006.01) | |
| A61F 5/56 | (2006.01) | |
| A61M 21/00 | (2006.01) | |
| G06F 1/16 | (2006.01) | |
| A61B 5/145 | (2006.01) | |
| A61B 5/026 | (2006.01) | |

(52) U.S. Cl.
CPC ............ *A61B 5/024* (2013.01); *A61B 5/0205* (2013.01); *A61B 5/02028* (2013.01); *A61B 5/02055* (2013.01); *A61B 5/02108* (2013.01); *A61B 5/02116* (2013.01); *A61B 5/02125* (2013.01); *A61B 5/02225* (2013.01); *A61B 5/02233* (2013.01); *A61B 5/02438* (2013.01); *A61B 5/08* (2013.01); *A61B 5/0816* (2013.01); *A61B 5/1118* (2013.01); *A61B 5/316* (2021.01); *A61B 5/352* (2021.01); *A61B 5/4818* (2013.01); *A61B 5/4836* (2013.01); *A61B 5/4884* (2013.01); *A61B 5/681* (2013.01); *A61B 5/6801* (2013.01); *A61B 5/6824* (2013.01); *A61B 5/721* (2013.01); *A61B 5/7221* (2013.01); *A61B 5/7239* (2013.01); *A61B 5/7275* (2013.01); *A61B 5/7278* (2013.01); *A61B 5/7282* (2013.01); *A61B 5/742* (2013.01); *A61B 5/743* (2013.01); *A61B 5/746* (2013.01); *A61F 5/56* (2013.01); *A61M 16/024* (2017.08); *A61M 21/00* (2013.01); *G06F 1/163* (2013.01); *G16H 10/40* (2018.01); *G16H 50/20* (2018.01); *A61B 5/026* (2013.01); *A61B 5/02141* (2013.01); *A61B 5/14532* (2013.01); *A61B 5/14542* (2013.01); *A61B 5/4806* (2013.01); *A61B 5/683* (2013.01); *A61B 5/7203* (2013.01); *A61B 5/7257* (2013.01); *A61B 2560/0242* (2013.01); *A61B 2562/029* (2013.01); *A61M 2021/0022* (2013.01); *A61M 2021/0027* (2013.01); *A61M 2021/0044* (2013.01); *A61M 2021/0083* (2013.01)

(56) References Cited

U.S. PATENT DOCUMENTS

| | | |
|---|---|---|
| 5,749,366 A | 5/1998 | Odagiri et al. |
| 5,772,601 A | 6/1998 | Oka et al. |
| 5,836,884 A * | 11/1998 | Ohio ................ A61B 5/02007 600/485 |
| 5,857,975 A | 1/1999 | Golub |
| 5,865,756 A | 2/1999 | Peel, III |
| 5,941,837 A | 8/1999 | Amano et al. |
| 5,980,464 A | 11/1999 | Tsuda |
| 6,030,342 A | 2/2000 | Amano et al. |
| 6,042,549 A | 3/2000 | Amano et al. |
| 6,081,742 A | 6/2000 | Amano et al. |
| 6,091,973 A | 7/2000 | Colla et al. |
| 6,095,984 A | 8/2000 | Amano et al. |
| 6,126,595 A | 10/2000 | Amano et al. |
| 6,287,262 B1 | 9/2001 | Amano et al. |
| 6,293,915 B1 | 9/2001 | Amano et al. |
| 6,331,159 B1 | 12/2001 | Amano et al. |
| 6,334,850 B1 | 1/2002 | Amano et al. |
| 6,361,501 B1 | 3/2002 | Amano et al. |
| 6,443,906 B1 | 9/2002 | Ting et al. |
| 6,554,763 B1 | 4/2003 | Amano et al. |
| 6,955,648 B2 | 10/2005 | Mozayeni et al. |
| 2002/0173726 A1 | 11/2002 | Narimatsu |
| 2003/0000522 A1 | 1/2003 | Lynn et al. |
| 2003/0004421 A1 | 1/2003 | Ting et al. |
| 2003/0004423 A1 | 1/2003 | Lavie et al. |
| 2003/0088184 A1 | 5/2003 | Kelly |
| 2003/0149369 A1 | 8/2003 | Gallant et al. |
| 2003/0163034 A1 | 8/2003 | Dekker |
| 2003/0204143 A1 | 10/2003 | Lin |
| 2003/0204144 A1 | 10/2003 | Lin |
| 2004/0044276 A1 | 3/2004 | Arnold |
| 2004/0176692 A1 | 9/2004 | Kario et al. |
| 2004/0210143 A1 | 10/2004 | Gallant et al. |
| 2005/0075531 A1 | 4/2005 | Loeb et al. |
| 2005/0096557 A1 | 5/2005 | Vosburgh et al. |
| 2005/0187480 A1 | 8/2005 | Kario et al. |
| 2006/0036126 A1* | 2/2006 | Ross ...................... A61M 1/12 600/16 |
| 2006/0142663 A1 | 6/2006 | Sawanoi et al. |
| 2006/0200011 A1 | 9/2006 | Suzuki et al. |
| 2007/0021673 A1 | 1/2007 | Arbel et al. |
| 2007/0118028 A1 | 5/2007 | Kitajima et al. |
| 2007/0282227 A1 | 12/2007 | Nanba et al. |
| 2008/0027331 A1 | 1/2008 | Suzuki et al. |
| 2008/0064965 A1 | 3/2008 | Jay et al. |
| 2008/0200774 A1 | 8/2008 | Luo |
| 2008/0262362 A1 | 10/2008 | Kolluri et al. |
| 2008/0294021 A1 | 11/2008 | Lin et al. |
| 2009/0124914 A1 | 5/2009 | Kuo et al. |
| 2009/0216132 A1 | 8/2009 | Orbach |
| 2009/0227425 A1 | 9/2009 | Shirasaki et al. |
| 2010/0121207 A1 | 5/2010 | Moersdorf et al. |
| 2010/0130874 A1 | 5/2010 | Joeken |
| 2010/0222650 A1 | 9/2010 | Tanishima et al. |
| 2010/0228139 A1 | 9/2010 | Nanba et al. |
| 2010/0268097 A1 | 10/2010 | Hatib et al. |
| 2010/0298721 A1 | 11/2010 | Kim et al. |
| 2011/0077534 A1 | 3/2011 | Kobayashi et al. |
| 2011/0077536 A1 | 3/2011 | Kubo |
| 2011/0098540 A1 | 4/2011 | Tanishima et al. |
| 2011/0152651 A1 | 6/2011 | Berkow |
| 2011/0166458 A1 | 7/2011 | Gallant et al. |
| 2011/0190643 A1 | 8/2011 | Zhang et al. |
| 2011/0224748 A1* | 9/2011 | Lippert .................. G16H 40/63 607/7 |
| 2011/0230729 A1 | 9/2011 | Shirasaki et al. |
| 2012/0029361 A1 | 2/2012 | Addison et al. |
| 2012/0108983 A1 | 5/2012 | Banet et al. |
| 2012/0125337 A1 | 5/2012 | Asanoi |
| 2013/0053664 A1 | 2/2013 | Jian et al. |
| 2013/0085079 A1 | 4/2013 | Gill et al. |
| 2013/0184545 A1* | 7/2013 | Blomqvist ............ A61B 5/686 600/325 |
| 2014/0018687 A1 | 1/2014 | Mano |

(56) References Cited

U.S. PATENT DOCUMENTS

| | | |
|---|---|---|
| 2014/0058220 A1 | 2/2014 | LeBoeuf et al. |
| 2014/0081101 A1 | 3/2014 | Shirasaki et al. |
| 2014/0163399 A1 | 6/2014 | Gallant et al. |
| 2014/0213858 A1 | 7/2014 | Presura et al. |
| 2014/0247970 A1 | 9/2014 | Taylor |
| 2014/0257124 A1 | 9/2014 | Morita |
| 2014/0275937 A1 | 9/2014 | Goedje et al. |
| 2014/0276071 A1 | 9/2014 | Hunziker et al. |
| 2014/0276123 A1 | 9/2014 | Yang |
| 2014/0303509 A1 | 10/2014 | Campbell |
| 2015/0099991 A1 | 4/2015 | Yamaguchi et al. |
| 2015/0109124 A1 | 4/2015 | He et al. |
| 2015/0164351 A1 | 6/2015 | He et al. |
| 2015/0168423 A1 | 6/2015 | Gill et al. |
| 2015/0196209 A1 | 7/2015 | Morris et al. |
| 2015/0245772 A1 | 9/2015 | Kawamoto et al. |
| 2015/0305632 A1 | 10/2015 | Najarian et al. |
| 2016/0058385 A1 | 3/2016 | Ajima |
| 2017/0209052 A1 | 7/2017 | Nakamura |
| 2017/0209074 A1 | 7/2017 | Siu et al. |
| 2017/0224227 A1 | 8/2017 | Kitagawa et al. |
| 2018/0028075 A1 | 2/2018 | Presura et al. |
| 2018/0078157 A1 | 3/2018 | Yang |
| 2018/0333056 A1 | 11/2018 | Chou |
| 2019/0083723 A1 | 3/2019 | Asanoi |
| 2020/0166523 A1 | 5/2020 | Gill et al. |

FOREIGN PATENT DOCUMENTS

| | | |
|---|---|---|
| CN | 1195277 A | 10/1998 |
| CN | 1199347 A | 11/1998 |
| CN | 1243425 A | 2/2000 |
| CN | 1430484 A | 7/2003 |
| CN | 1568158 A | 1/2005 |
| CN | 1627916 A | 6/2005 |
| CN | 1785117 A | 6/2006 |
| CN | 101081167 A | 12/2007 |
| CN | 101193588 A | 6/2008 |
| CN | 101288586 A | 10/2008 |
| CN | 101321490 A | 12/2008 |
| CN | 101785666 A | 7/2010 |
| CN | 102038495 A | 5/2011 |
| CN | 102481127 A | 5/2012 |
| CN | 102697506 A | 10/2012 |
| CN | 103781414 A | 5/2014 |
| CN | 103959060 A | 7/2014 |
| CN | 104382569 A | 3/2015 |
| CN | 104511150 A | 4/2015 |
| CN | 104665821 A | 6/2015 |
| CN | 104873182 A | 9/2015 |
| CN | 105054918 A | 11/2015 |
| CN | 105361858 A | 3/2016 |
| CN | 105377124 A | 3/2016 |
| EP | 0872255 A1 | 10/1998 |
| EP | 0875199 A1 | 11/1998 |
| EP | 1057450 A2 | 12/2000 |
| EP | 1150604 A1 | 11/2001 |
| EP | 1334693 A1 | 8/2003 |
| EP | 2759257 A1 | 7/2014 |
| JP | H08-317912 A | 12/1996 |
| JP | H11-128186 A | 5/1999 |
| JP | 2002-536104 A | 10/2002 |
| JP | 2002336210 A | 11/2002 |
| JP | 2003-325465 A | 11/2003 |
| JP | 2004-121865 A | 4/2004 |
| JP | 2004-136105 A | 5/2004 |
| JP | 2004-223271 A | 8/2004 |
| JP | 2004-261452 A | 9/2004 |
| JP | 2005-237472 A | 9/2005 |
| JP | 2005-532111 A | 10/2005 |
| JP | 2006-212218 A | 8/2006 |
| JP | 2007-117591 A | 5/2007 |
| JP | 2008-536545 A | 9/2008 |
| JP | 2010-22689 A | 2/2010 |
| JP | 2010-200901 A | 9/2010 |
| JP | 2012-521223 A | 9/2012 |
| JP | 2013-517908 A | 5/2013 |
| JP | 2014-18272 A | 2/2014 |
| JP | 2014-171589 A | 9/2014 |
| JP | 2016-87003 A | 5/2016 |
| WO | 97/38626 A1 | 10/1997 |
| WO | 99/26529 A1 | 6/1999 |
| WO | 2004/004558 A1 | 1/2004 |
| WO | 2008/001607 A1 | 1/2008 |
| WO | 2009/020114 A1 | 2/2009 |
| WO | 2009/076126 A1 | 6/2009 |
| WO | 2014/171465 A1 | 10/2014 |
| WO | 2015/178439 A2 | 11/2015 |
| WO | 2016/017579 A1 | 2/2016 |
| WO | 2016/018906 A1 | 2/2016 |
| WO | 2018/017425 A1 | 1/2018 |

OTHER PUBLICATIONS

Written Opinion issued in International Application No. PCT/JP2017/015274, dated Jun. 20, 2017, (5 pages).
International Preliminary Report on Patentability issued in Application No. PCT/JP2017/015274, dated Oct. 16, 2018 (6 pages).
International Search Report issued in Application No. PCT/JP2017/015275, dated Jul. 4, 2017 (2 pages).
Written Opinion issued in International Application No. PCT/JP2017/015275, dated Jul. 4, 2017 (7 pages).
International Preliminary Report on Patentability issued in Application No. PCT/JP2017/015275, dated Oct. 16, 2018 (8 pages).
International Search Report issued in Application No. PCT/JP2017/015276, dated Jun. 27, 2017 (2 pages).
Written Opinion issued in International Application No. PCT/JP2017/015276, dated Jun. 27, 2017 (4 pages).
International Preliminary Report on Patentability issued in Application No. PCT/JP2017/015276, dated Oct. 16, 2018 (5 pages).
International Search Report issued in Application No. PCT/JP2017/015277, dated Jul. 18, 2017 (2 pages).
Written Opinion issued in International Application No. PCT/JP2017/015277, dated Jul. 18, 2017 (4 pages).
International Preliminary Report on Patentability issued in Application No. PCT/JP2017/015277, dated Oct. 16, 2018 (5 pages).
International Search Report issued in Application No. PCT/JP2017/015278, dated Jul. 11, 2017 (2 pages).
Written Opinion issued in International Application No. PCT/JP2017/015278, dated Jul. 11, 2017 (4 pages).
International Preliminary Report on Patentability issued in Application No. PCT/JP2017/015278, dated Oct. 16, 2018 (5 pages).
International Search Report issued in Application No. PCT/JP2017/015279, dated Jul. 11, 2017 (1 page).
Written Opinion issued in International Application No. PCT/JP2017/015279, dated Jul. 11, 2017 (4 pages).
International Preliminary Report on Patentability issued in Application No. PCT/JP2017/015279, dated Oct. 16, 2018 (5 pages).
International Search Report issued in Application No. PCT/JP2017/015280, dated Jul. 18, 2017 (2 pages).
Written Opinion issued in International Application No. PCT/JP2017/015280, dated Jul. 18, 2017 (4 pages).
International Preliminary Report on Patentability issued in Application No. PCT/JP2017/015280, dated Oct. 16, 2018 (5 pages).
International Search Report issued in Application No. PCT/JP2017/015281, dated Jul. 18, 2017 (2 pages).
Written Opinion issued in International Application No. PCT/JP2017/015281, dated Jul. 18, 2017 (3 pages).
International Preliminary Report on Patentability issued in Application No. PCT/JP2017/015281, dated Oct. 16, 2018 (4 pages).
International Search Report issued in Application No. PCT/JP2017/015282, dated Jul. 11, 2017 (1 page).
Written Opinion issued in International Application No. PCT/JP2017/015282, dated Jul. 11, 2017 (3 pages).
International Preliminary Report on Patentability issued in Application No. PCT/JP2017/015282, dated Oct. 16, 2018 (4 pages).
International Search Report issued in Application No. PCT/JP2017/015283, dated Jul. 11, 2017 (1 page).

(56) References Cited

OTHER PUBLICATIONS

Written Opinion issued in International Application No. PCT/JP2017/015283, dated Jul. 11, 2017 (3 pages).
International Preliminary Report on Patentability issued in Application No. PCT/JP2017/015283, dated Oct. 16, 2018 (4 pages).
International Search Report issued in Application No. PCT/JP2017/015284, dated Jun. 27, 2017 (2 pages).
Written Opinion issued in International Application No. PCT/JP2017/015284, dated Jun. 27, 2017 (3 pages).
International Preliminary Report on Patentability issued in Application No. PCT/JP2017/015284, dated Oct. 16, 2018 (4 pages).
Extended European Search Report issued in Application No. 17782512.2, dated Jan. 21, 2020 (8 pages).
Notice of Reasons for Refusal issued in Japanese Application No. 2018-512086, dated Feb. 24, 2020 (5 pages).
Extended European Search Report issued in Application No. 17782508.0, dated Sep. 30, 2019 (8 pages).
Extended European Search Report issued in Application No. 17782507.2, dated Sep. 30, 2019 (8 pages).
Extended European Search Report issued in Application No. 17782506.4, dated Oct. 29, 2019 (9 pages).
Extended European Search Report issued in Application No. 17782509.8, dated Nov. 4, 2019 (8 pages).
Extended European Search Report issued in Application No. 17782514.8, dated Nov. 4, 2019 (9 pages).
Extended European Search Report issued in Application No. 17782515.5, dated Nov. 7, 2019 (9 pages).
Extended European Search Report issued in Application No. 17782510.6, dated Nov. 7, 2019 (9 pages).
Extended European Search Report issued in Application No. 17782511.4, dated Nov. 7, 2019 (9 pages).
Extended European Search Report issued in Application No. 17782513.0, dated Nov. 13, 2019 (8 pages).
Extended European Search Report issued in Application No. 17782516.3, dated Nov. 12, 2019 (8 pages).
Office Action issued in Chinese Application No. 201780022567.0; dated Jul. 28, 2020 (20 pages).
Office Action in the counterpart Japanese Patent Application No. 2018-512086 dated May 26, 2020 (8 pages).
Office Action issued in Chinese Application No. 201780022565.1; dated Sep. 1, 2020 (25 pages).
Office Action issued in Chinese Application No. 201780022527.6; dated Oct. 10, 2020 (17 pages).
Office Action issued in U.S. Appl. No. 16/092,060, dated Mar. 25, 2021 (50 pages).
McGee; "Evidence-Based Physical Diagnosis;" ScienceDirect; 4th Edition; 2017 (4 pages).
Office Action issued in Chinese Application No. 201780022529.5; dated Jan. 5, 2021 (19 pages).
Office Action issued in Chinese Application No. 201780022537.X, dated Feb. 25, 2021 (18 pages).
Office Action issued in Chinese Application No. 201780022567.0, dated Mar. 1, 2021 (16 pages).
Office Action issued in Chinese Application No. 201780022528.0, dated Mar. 2, 2021 (10 pages).
Office Action issued in Chinese Application No. 201780022566.6; dated Aug. 4, 2020 (19 pages).
Office Action issued in Chinese Application No. 201780022528.0; dated Aug. 31, 2020 (19 pages).
Office Action issued in Chinese Application No. 201780022530.8; dated Oct. 9, 2020 (16 pages).
Office Action issued in Chinese Application No. 201780022568.5; dated Oct. 10, 2020 (22 pages).
Office Action issued in Japanese Application No. 2018-512086; dated Oct. 6, 2020 (5 pages).
P. Boudreau et al. "Circadian Variation of Heart Rate Variability Across Sleep Stages" Sleep, vol. 36, No. 12, 2013 (10 pages).
Q. Han et al. "The Method of Simultaneously Removing Breathing Baseline and High-frequency Noise in Pulse Wave Signal" Chinese Journal of Medical Physics, vol. 31, No. 2 (5 pages).
W. Hu et al. "Diastolic Blood Pressure Rises with the Exacerbation of Obstructive Sleep Apnea in Males" Obesity, vol. 25, No. 11; Nov. 2017 (9 pages).
Office Action issued in U.S. Appl. No. 16/092,134; dated Jun. 23, 2021 (84 pages).
Office Action issued in U.S. Appl. No. 16/092,076; dated Jun. 28, 2021 (78 pages).
Office Action issued in U.S. Appl. No. 16/092,060; dated Jul. 9, 2021 (30 pages).
Restriction Requirement issued in U.S. Appl. No. 16/092,136; dated Jul. 12, 2021 (7 pages).
Office Action issued in U.S. Appl. No. 16/092,095; dated Jul. 26, 2021 (66 pages).
Office Action issued in U.S. Appl. No. 16/092,167; dated Aug. 3, 2021 (88 pages).
Office Action issued in U.S. Appl. No. 16/092,113; dated Aug. 4, 2021 (94 pages).
Du Jun, "Blood pressure changes and heart rate variability in sleep apnea at night", Foreign Medical Neurology Neurosurgery, vol. 24, No. 5,1997, pp. 271-272 (2 pages).
Office Action issued in Chinese Application No. 201780022781.6; dated Jul. 13, 2020 (17 pages).
Office Action issued in Chinese Application No. 201780022529.5; dated Jul. 17, 2020 (20 pages).
Office Action issued in Chinese Application No. 201780022536.5; dated Jul. 27, 2020 (23 pages).

* cited by examiner

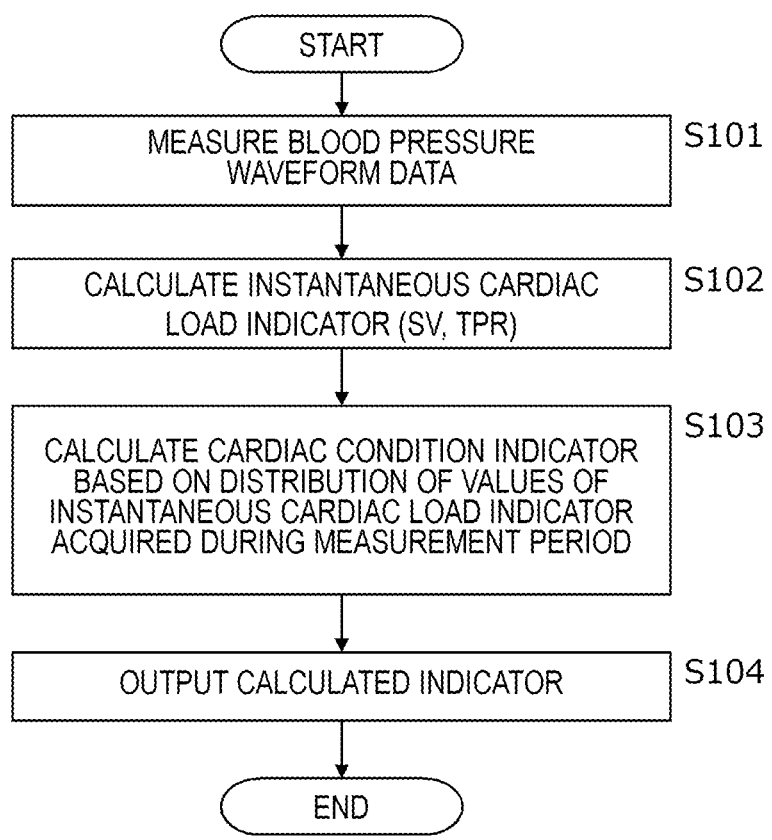

BIOLOGICAL INFORMATION ANALYSIS DEVICE, SYSTEM, AND PROGRAM

TECHNICAL FIELD

The present invention relates to technology for acquiring useful information from a blood pressure waveform that has been measured.

RELATED ART

There is a known technology for measuring changes in the internal pressure of a radial artery and recording the shape of a pressure pulse wave (blood pressure waveform). Patent Document 1 (JP 2008-61824A) discloses that a blood pressure waveform is measured using a tonometry method, and pieces of information such as an AI (Augmentation Index) value, a pulse wave period, a baseline fluctuation rate, sharpness, and an ET (Ejection Time) are acquired from the blood pressure waveform. Also, Patent Document 2 (JP 2005-532111A) discloses that a blood pressure waveform is measured using a wristwatch-type blood pressure meter, in which a mean arterial pressure, a mean systolic pressure, a mean diastolic pressure, a mean systolic pressure indicator, and a mean diastolic pressure indicator are calculated from the blood pressure waveform, and an alert is output when any of these values deviates from a reference value.

RELATED ART DOCUMENTS

Patent Documents

Patent Document 1: JP 2008-61824A
Patent Document 2: JP 2005-532111A

SUMMARY OF THE INVENTION

Problem to be Solved by the Invention

The inventors of the present invention have worked hard to develop a blood pressure measurement device that can accurately measure an ambulatory blood pressure waveform for each heartbeat, and to put such a device into practical use. Through experiments performed on subjects during the development phase, the inventors have found that various kinds of useful information can be extracted from data regarding ambulatory blood pressure waveforms that have been consecutively measured.

Several kinds of loads on the heart, such as afterload and preload, are known as factors that promote cardiac hypertrophy and cardiac expansion. Afterload can be evaluated using a stroke volume (SV, which is also referred to as "cardiac output"), and preload can be evaluated using total peripheral resistance (TPR). However, the blood pressure measurement devices disclosed in the documents above measure afterload and preload for each heartbeat, and the subject needs to be in a resting state. Therefore, the devices cannot measure ambulatory blood pressure when the heart is actually under a load. There also is a problem in which the devices cannot perform measurement for a long period of time (e.g. overnight).

The inventors of the present invention have found that it is possible to evaluate a cardiac state and the risk of cardiac diseases occurring, based on pieces of ambulatory blood pressure waveform data that have been consecutively measured.

The present invention aims to provide a novel technology for evaluating a cardiac state.

Means for Solving the Problems

To achieve the above-described aim, the present invention employs the following configurations.

A biological information analysis device according to one aspect of the present invention includes: an indicator extraction unit configured to extract an indicator indicating a cardiac state (hereinafter referred to as a cardiac state indicator), from data regarding blood pressure waveforms that are consecutively measured by a sensor that is configured to be worn on a body part of a user and to be capable of non-invasively measuring a blood pressure waveform for each heartbeat; and a processing unit configured to output the indicator extracted by the indicator extraction unit. The indicator extraction unit is configured to extract a value of the cardiac load indicator for each heartbeat, from the data regarding blood pressure waveforms, and calculate the indicator indicating the cardiac state, based on characteristics related to distribution of values of the cardiac load indicator corresponding to a plurality of heartbeats.

In this aspect, a stroke volume (SV) or a value determined based on the stroke volume may be employed as the cardiac load indicator. The stroke volume is the volume of blood ejected from a ventricle per contraction, and is an indicator indicating preload. In the following description, the stroke volume per heartbeat is also referred to as an instantaneous stroke volume.

The indicator extraction unit in the present aspect may be configured to determine the cardiac state indicator based on the frequency (the proportion of the frequency) with which the value of the instantaneous stroke volume exceeds a first threshold value in the distribution of values of the instantaneous stroke volume. The cardiac state indicator may be the frequency itself or a value determined based on the frequency. The first threshold value may be determined based on the maximum value of the instantaneous stroke volume of the user. For example, a value within the range of 60% to 99%, preferably a value within the range of 70% to 90%, or further preferably a value within the range of 75% to 85% of the maximum instantaneous stroke volume may be employed as the first threshold value. The maximum instantaneous stroke volume may be determined as the maximum value of the instantaneous stroke volume acquired during the aforementioned consecutive measurement, or determined using another method.

It can be said that a state in which the instantaneous stroke volume is greater than the first threshold value is a state in which excessive preload has occurred, and therefore the frequency of occurrence thereof is related to the risk of cardiac expansion occurring. That is, it is possible to evaluate the risk of cardiac expansion occurring, using the cardiac state indicator calculated as described above.

The indicator extraction unit in the present aspect may be configured to determine the cardiac state indicator based on the frequency (the proportion of the frequency) with which the value of the instantaneous stroke volume falls below a second threshold value in the distribution of values of the instantaneous stroke volume. The cardiac state indicator may be the frequency itself or a value determined based on the frequency. The second threshold value to be used may be the same predetermined value for every user, or unique to each user.

It can be said that a state in which the instantaneous stroke volume is smaller than the second threshold value is a state in which preload is excessively low, and the frequency of occurrence thereof is related to the risk of a blood clot being formed. That is, it is possible to evaluate the risk of a blood clot being formed, using the cardiac state indicator calculated as described above.

The indicator extraction unit in the present aspect may determine the cardiac state indicator based on the maximum value of the stroke volume (the maximum instantaneous stroke volume) in the distribution. The cardiac state indicator may be the maximum value itself or a value determined based on the maximum value. Note that it is preferable that blood pressure waveforms are measured by the sensor while the user is performing exercise at an intensity that is no less than a predetermined intensity.

The maximum value (the saturation point) of the instantaneous stroke volume is related to the capacity of the heart, and a decrease therein is related to the risk of cardiac hypertrophy occurring. That is, it is possible to evaluate the risk of cardiac hypertrophy occurring, using the cardiac state indicator calculated as described above.

In the present aspect, a total peripheral resistance (TPR) or a value determined based on a total peripheral resistance may be employed as the cardiac load indicator. Total peripheral resistance is the resistance against the flow of blood in a blood vessel, and is an indicator indicating afterload. Total peripheral resistance is also referred to as systemic vascular resistance (SVR). In the following description, a total peripheral resistance per heartbeat is also referred to as an instantaneous total peripheral resistance or an instantaneous TPR.

The indicator extraction unit in the present aspect may be configured to determine the cardiac state indicator based on the frequency (the proportion of the frequency) with which the value of the instantaneous TPR exceeds a third threshold value in the distribution of values of the instantaneous TPR. The cardiac state indicator may be the frequency itself or a value determined based on the frequency. The third threshold value to be used may be the same predetermined value for every user, or unique to each user.

It can be said that a state in which the instantaneous total peripheral resistance is greater than the third threshold value is a state in which excessive afterload has occurred, and therefore the frequency of occurrence thereof is related to the risk of cardiac hypertrophy occurring. That is, it is possible to evaluate the risk of cardiac hypertrophy occurring, using the cardiac state indicator calculated as described above.

The processing unit in the present aspect may be configured to output temporal changes in values of the cardiac load indicator corresponding to a plurality of heartbeats, and an indicator indicating the cardiac state. By outputting temporal changes in the cardiac load indicator, it is possible to make it easier to ascertain when a cardiac load that may cause a cardiac disease has occurred.

The processing unit in the present aspect may be configured to acquire, from a second sensor, data indicating at least one of the user's body movement and the state of the environment during measurement of blood pressure waveforms, and output temporal changes in the cardiac load indicator in association with at least one of the user's body movement and the state of the environment. Such an output makes it possible to ascertain the relationship between the cardiac load indicator and the state of the user or the environment, and makes it easier to identify the cause of an increase in cardiac load.

The processing unit in the present aspect may be configured to acquire, from a second sensor, time-series data indicating the state of the environment during measurement of blood pressure waveforms, and output the cardiac load indicator and the state of the environment in association with each other. Data indicating the state of the environment may be any data as long as it is data regarding an influencing factor that is presumably related to cardiac load or the risk of a cardiac disease occurring. The processing unit may output time-series data regarding the cardiac load indicator and time-series data regarding the influencing factor superimposed on each other. Also, the processing unit may output a graph that shows an influencing factor and a cardiac load indicator at the same point in time as a first coordinate value and a second coordinate value, respectively. Such an output makes it easier to identify the cause of an increase in cardiac load.

A biological information analysis system according to one aspect of the present invention is a system including: a sensor that is configured to be worn on a body part of a user and to be capable of non-invasively measuring a blood pressure waveform for each heartbeat; and a biological information analysis device configured to analyze biological information, using data regarding blood pressure waveforms consecutively measured by the sensor.

A program according to the present invention is a program that causes a processor to function as the indicator extraction unit and the processing unit of the biological information analysis device.

Note that the present invention can be interpreted as a biological information analysis device or system that is provided with at least one of the above-described configurations or at least one of the above-described functions. The present invention can also be interpreted as a biological information analysis method that includes at least part of the above-described processing, or a program that causes a computer to execute such a method, or a computer-readable recording medium on which such a program is recorded in a non-transitory manner. The present invention can be formed by combining the above-described configurations and the above-described kinds of processing with each other unless no technical inconsistency occurs.

Effects of the Invention

According to the present invention, it is possible to provide a novel technology for evaluating a cardiac state.

BRIEF DESCRIPTION OF THE DRAWINGS

FIG. 8 is a flowchart for indicator calculation processing according to Examples 1 and 2.

EMBODIMENTS OF THE INVENTION

The following describes a preferred embodiment of the present invention with reference to the drawings. Note that the following descriptions of components may be modified as appropriate depending on the configuration of a device to which the present invention is applied, and on various conditions, and the scope of the present invention is not intended to be limited to the following descriptions.

Biological Information Analysis System

Figure 1:
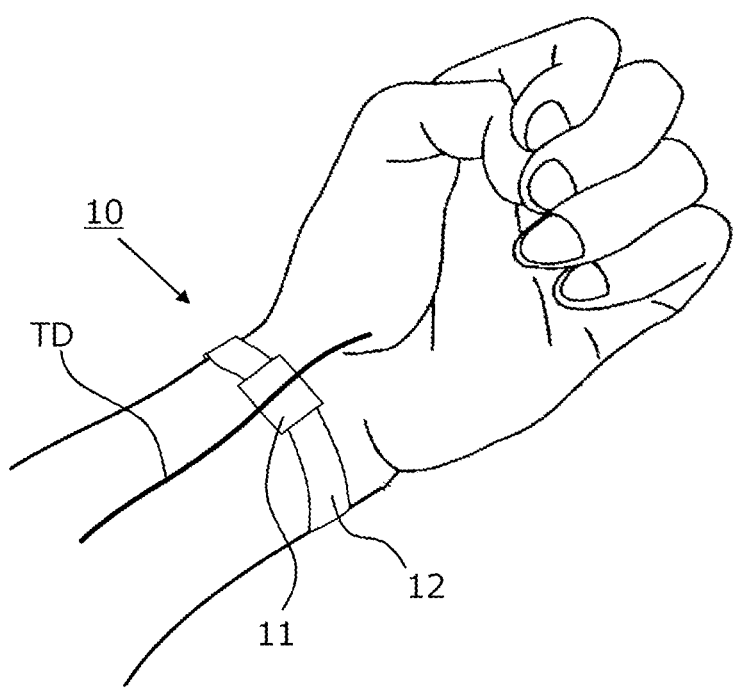
FIG. 1 shows a schematic external configuration of a biological information analysis system 10.

FIG. 1 shows a schematic external configuration of a biological information analysis system 10 according to an embodiment of the present invention. FIG. 1 shows a state in which the biological information analysis system 10 is worn on the left wrist. The biological information analysis system 10 includes a main body 11 and a belt 12 that is fixed to the main body 11. The biological information analysis system 10 is a so-called wearable device, and is worn such that the main body 11 is in contact with the skin on the palm side of the wrist, and the main body 11 is located over a radial artery TD that lies beneath the skin. Although the device is configured to be worn on the radial artery TD in the present embodiment, the device may be configured to be worn on another superficial artery.

Figure 2:
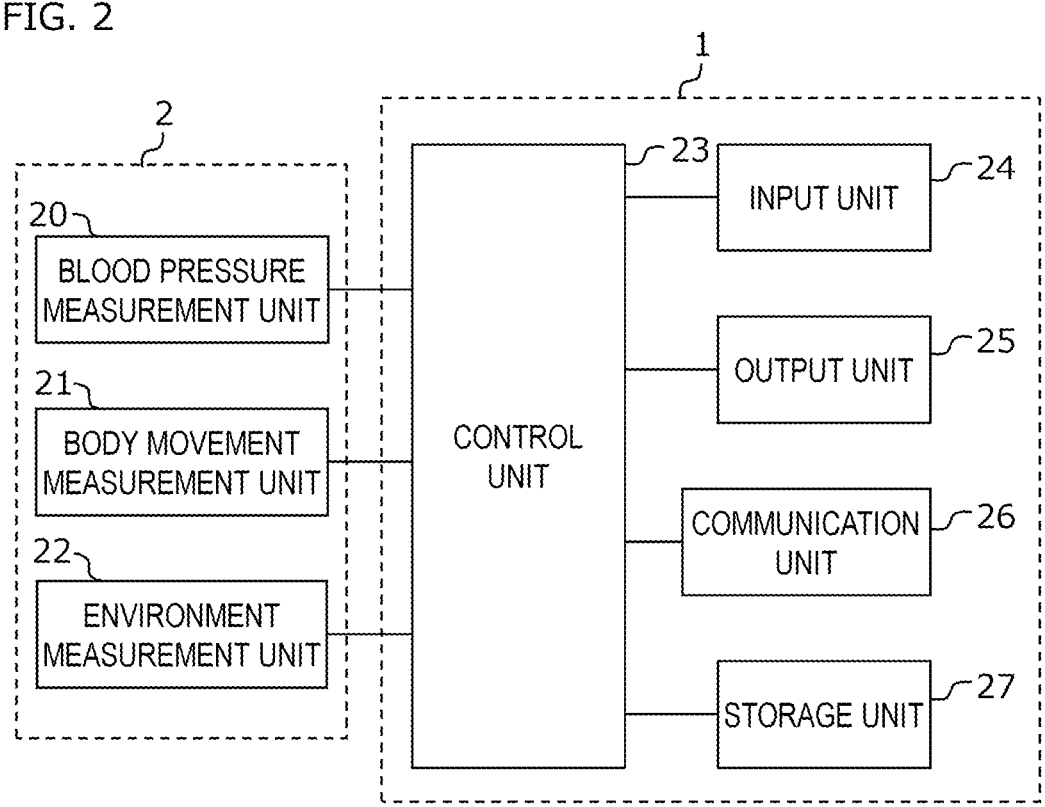
FIG. 2 is a block diagram showing a hardware configuration of the biological information analysis system 10.

FIG. 2 is a block diagram showing a hardware configuration of the biological information analysis system 10. In general, the biological information analysis system 10 includes a measurement unit 2 and the biological information analysis device 1. The measurement unit 2 is a device that performs measurement to acquire information that is used to analyze biological information, and includes a blood pressure measurement unit 20, a body movement measurement unit 21, and an environment measurement unit 22. However, note that the configuration of the measurement unit 2 is not limited to that shown in FIG. 2. For example, a unit that measures biological information other than blood pressure or a body movement (e.g. body temperature, blood-sugar level, or brain waves) may be added. Also, any unit that is not used in the example described below is not an essential component, and may be omitted from the biological information analysis system 10. The biological information analysis device 1 is a device that analyzes biological information based on information acquired from the measurement unit 2, and includes a control unit 23, an input unit 24, an output unit 25, a communication unit 26, and a storage unit 27. The units 20 to 27 are connected to each other so that signals can be exchanged between them via a local bus or other signal lines. The biological information analysis system 10 also includes a power supply (a battery), which is not shown.

The blood pressure measurement unit 20 measures a pressure pulse wave from the radial artery TD by using a tonometry method. The tonometry method is for forming a flat area in the artery TD by pressing the artery from the skin with appropriate pressure, adjusting the balance between the internal pressure and the external pressure of the artery, and non-invasively measuring the pressure pulse wave using a pressure sensor.

The body movement measurement unit 21 includes a tri-axis acceleration sensor, and measures the movement of the user's body (body movement) using this sensor. The body movement measurement unit 21 may include a circuit that converts the format of an output from the tri-axis acceleration sensor into a format that is readable to the control unit 23.

The environment measurement unit 22 measures environmental information that may affect mental and physical conditions of the user (in particular the blood pressure). The environment measurement unit 22 may include, for example, an atmospheric temperature sensor, a humidity sensor, an illuminance sensor, an altitude sensor, a position sensor, and so on. The environment measurement unit 22 may include a circuit that converts the format of outputs from these sensors and so on into a format that is readable to the control unit 23.

The control unit 23 performs various kinds of processing, such as controlling each unit of the biological information analysis system 10, acquiring data from the measurement unit 2, storing the acquired data in the storage unit 27, processing and analyzing data, and inputting and outputting data. The control unit 23 includes a hardware processor (hereinafter referred to as the "CPU") a ROM (Read Only Memory), a RAM (Random Access Memory), and so on. Processing that is performed by the control unit 23, which will be described later, is realized by the CPU reading and executing a program stored in the ROM or the storage unit 27. The RAM functions as a work memory that is used by the control unit 23 when performing various kinds of processing. Although acquisition of data from the measurement unit 2 and the storing of data in the storage unit 27 are performed by the control unit 23 in the present embodiment, it is possible to employ a configuration in which the measurement unit 2 directly stores (writes) data in the storage unit 27.

Each of the constituent components of the embodiment such as a measurement unit, an indicator extraction unit, a processing unit, a determination unit, a risk database, an input unit, an output unit, a case database, and so on may be implemented as pieces of hardware in the biological information analysis system 10. The indicator extraction unit, the processing unit, and the determination unit may receive an executable program stored in the storage unit 27, and execute the program. The indicator extraction unit, the processing unit, and the determination unit may receive data from the blood pressure measurement unit 20, the body movement measurement unit 21, the environment measurement unit 22, the input unit 24, the output unit 25, the communication unit 26, the storage unit 27, and so on as required. Databases such as the risk database and the case database may be implemented using the storage unit 27 and so on, and store pieces of information that are arranged such that a data search and data accumulation can be easily performed. Here, for example, the configuration, operations, and so on of the biological information analysis system 10 are disclosed in JP 2016-082069A. The contents of this disclosure are incorporated herein by reference. Also, the configuration, operations, and so on of the blood pressure measurement unit are disclosed in JP 2016-087003A. The contents of this disclosure are incorporated herein by reference.

The input unit 24 provides an operation interface for the user. For example, an operation button, a switch, a touch panel, and so on may be used.

The output unit 25 provides an interface that outputs information to the user. For example, a display device (such as a liquid crystal display) that outputs information using images, an audio output device or a beeper that outputs information using audio, an LED that outputs information by blinking, a vibration device that outputs information by vibrating, and so on may be used.

The communication unit 26 performs data communication with another device. Any data communication method such as a wireless LAN or Bluetooth (registered trademark) may be used.

The storage unit 27 is a storage medium that can store data and from which data can be read out, and stores programs that are to be executed by the control unit 23, pieces of measurement data acquired from the measurement units, and various kinds of data acquired by processing the pieces of measurement data, and so on. The storage unit 27 is a medium that accumulates pieces of information that are to be stored, through an electrical, magnetic, optical, mechanical, or chemical action. For example, a flash memory is used. The storage unit 27 may be a portable unit such as a memory card, or built into the biological information analysis system 10.

At least one unit or all units out of the body movement measurement unit 21, environment measurement unit 22, the control unit 23, the input unit 24, the output unit 25, and the storage unit 27 may be configured as a device that is separate from the main body 11. That is, as long as the blood pressure measurement unit 20 and the main body 11 that incorporates a circuit that controls the blood pressure measurement unit 20 are configured to be wearable on a wrist, the configurations of other units can be freely designed. If this is the case, the main body 11 cooperates with another unit via the communication unit 26. Various configurations can be conceived of. For example, the functions of the control unit 23, the input unit 24, and the output unit 25 may be realized using a smartphone application, and required data may be acquired from an activity monitor that has the functions of the body movement measurement unit 21 and the environment measurement unit 22. Also, a sensor that measures biological information other than blood pressure may be provided. For example, a sleep sensor, a pulse oximeter ($SpO_2$ sensor), a respiration sensor (a flow sensor), a blood-sugar level sensor, and the like may be combined.

Although the sensor (the blood pressure measurement unit 20) that measures blood pressure and the component (including the control unit 23 and so on) that performs processing to analyze blood pressure waveform data are provided in one device in the present embodiment, they may be provided in separate members. In the present embodiment, the component (including the control unit 23 and so on) that performs processing to analyze biological information is referred to as a biological information analysis device, and the device that includes the combination of the measurement unit and the biological information analysis device is referred to as a biological information analysis system. However, these names are given for descriptive purposes, and the measurement unit and the component that performs processing to analyze biological information may be referred to as a biological information analysis device as a whole, or other names may be used.

Measurement of Blood Pressure Waveform

Figure 3:
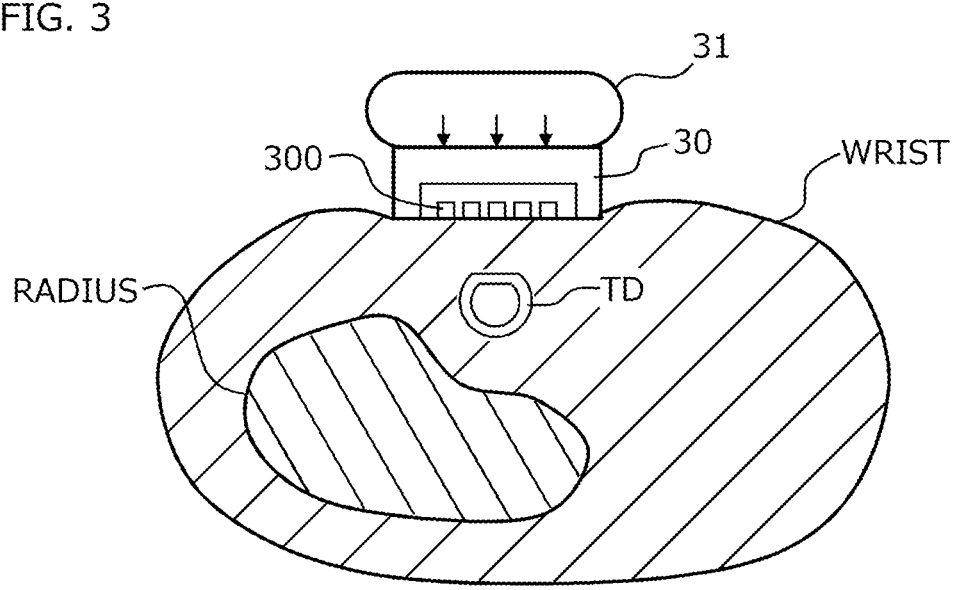
FIG. 3 is a cross-sectional view schematically showing a configuration of a blood pressure measurement unit 20 and a state in which measurement is performed.

FIG. 3 is a cross-sectional view schematically showing the configuration of the blood pressure measurement unit 20 and a state in which measurement is performed. The blood pressure measurement unit 20 includes a pressure sensor 30 and a pressurizing mechanism 31 for pressing the pressure sensor 30 against a wrist. The pressure sensor 30 includes a plurality of pressure detection elements 300. The pressure detection elements 300 detect pressure and convert the pressure into an electrical signal. For example, elements that utilize a piezoresistive effect may be preferably used. The pressurizing mechanism 31 includes, for example, an air bag and a pump that adjusts the internal pressure of the air bag. As a result of the control unit 23 controlling the pump to increase the internal pressure of the air bag, the air bag expands and the pressure sensor 30 is pressed against the surface of the skin. Note that the pressurizing mechanism 31 may be any mechanism as long as it can adjust the pressing force of the pressure sensor 30 applied to the surface of the skin, and is not limited to a mechanism that uses an air bag.

Upon the biological information analysis system 10 being worn on a wrist and activated, the control unit 23 controls the pressurizing mechanism 31 of the blood pressure measurement unit 20 to keep the pressing force of the pressure sensor 30 in an appropriate state (a tonometry state). Then, pressure signals detected by the pressure sensor 30 are sequentially acquired by the control unit 23. Pressure signals acquired from the pressure sensor 30 are generated by digitizing analogue physical amounts (e.g. voltage values) output by the pressure detection elements 300, through an A/D converter circuit or the like that employs a well-known technology. Preferable analogue values such as current values or resistance values may be employed as the analogue physical amounts, depending on the type of the pressure detection elements 300. Signal processing such as the aforementioned A/D conversion may be performed using a predetermined circuit provided in the blood pressure measurement unit 20, or performed by another unit (not shown) provided between the blood pressure measurement unit 20 and the control unit 23. Each pressure signal acquired by the control unit 23 corresponds to an instantaneous value of the internal pressure of the radial artery TD. Therefore, it is possible to acquire time-series data regarding blood pressure waveforms by acquiring pressure signals with time granularity and continuity that make it possible to ascertain a blood pressure waveform for each heartbeat. The control unit 23 stores the pressure signals sequentially acquired from the pressure sensor 30, in the storage unit 27, together with information regarding points in time at which the pressure signals were measured. The control unit 23 may store the acquired pressure signals in the storage unit 27 without change, or store the pressure signals in the storage unit 27 after performing required signal processing on the pressure signals. Required signal processing includes, for example, processing that is performed to calibrate each pressure signal such that the amplitude of the pressure signal matches the blood pressure value (e.g. the brachial blood pressure), processing that is performed to reduce or remove noise in each pressure signal, and so on.

Figure 4:
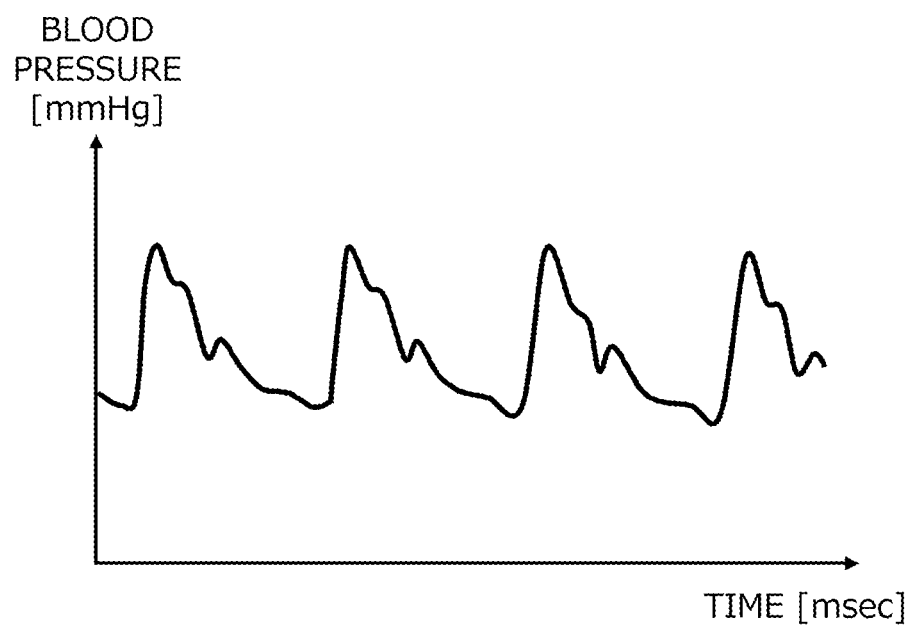
FIG. 4 shows a blood pressure waveform that is measured by the blood pressure measurement unit 20.

FIG. 4 shows a blood pressure waveform measured by the blood pressure measurement unit 20. The horizontal axis indicates time and the vertical axis indicates blood pressure. Although the sampling frequency may be set to any value, it is preferably set to be no less than 100 Hz so that characteristics of the shape of a waveform corresponding to one heartbeat can be reproduced. Typically, the period of one heartbeat is approximately one second, and therefore approximately one hundred or more data points can be acquired on a waveform corresponding to one heartbeat.

The blood pressure measurement unit 20 according to the present embodiment is advantageous in terms of the following.

The blood pressure measurement unit 20 can measure a blood pressure waveform for each heartbeat. As a result, it is possible to acquire various indicators related to blood pressure, the state of the heart, cardiovascular risks, and so on, based on the characteristics of the shape of the blood pressure waveform. In addition, it is possible to monitor for instantaneous values of blood pressure. Therefore, it is possible to instantaneously detect a blood pressure surge (a sudden rise in the blood pressure value), and to detect changes in blood pressure and irregularities in a blood pressure waveform that may occur in a very short period of time (corresponding to one to several heartbeats) without missing them.

As a portable blood pressure meter, a blood pressure meter that is to be worn on a wrist or an upper arm and employs an oscillometric method to measure blood pressure has come into practical use. However, a conventional portable blood pressure meter can only measure the mean value of blood pressure based on changes in the internal pressure of a cuff during a period of several seconds to a dozen or so seconds corresponding to a plurality of heartbeats, and cannot acquire time-series data regarding a blood pressure waveform for each heartbeat, unlike the blood pressure measurement unit 20 according to the present embodiment.

The blood pressure measurement unit 20 can record time-series data regarding blood pressure waveforms. By acquiring time-series data regarding blood pressure waveforms, and, for example, discerning characteristics of the blood pressure waveform related to temporal changes, or performing a frequency analysis on the time-series data to extract a specific frequency component, it is possible to acquire various indicators related to blood pressure, the state of the heart, cardiovascular risks, and so on.

The device employs a portable (wearable) type configuration, and less burden is placed on the user during measurement. Therefore, continuous measurement for a long time, and even 24-hour blood pressure monitoring, can be relatively easily performed. Also, since the device is of a portable type, changes in not only blood pressure under resting conditions, but also an ambulatory blood pressure (for example, during daily life or exercise) can be measured. As a result, it is possible to grasp how blood pressure is affected by behaviours in daily life (such as sleeping, eating, commuting, working, and taking medicine) and exercise, for example.

Conventional products are types of devices that measure blood pressure under resting conditions, with an arm or a wrist fixed to a blood pressure measurement unit, and cannot measure changes in blood pressure in daily life or during exercise, unlike the biological information analysis system 10 according to the present embodiment.

The blood pressure measurement unit 20 can be easily combined or linked with other sensors. For example, it is possible to make an evaluation of a cause-effect relationship or a composite evaluation with information that can be acquired by other sensors (e.g. a body movement, environmental information such as an atmospheric temperature, biological information such as $SpO_2$ and respiration information).

Biological Information Analysis Device

Figure 5:
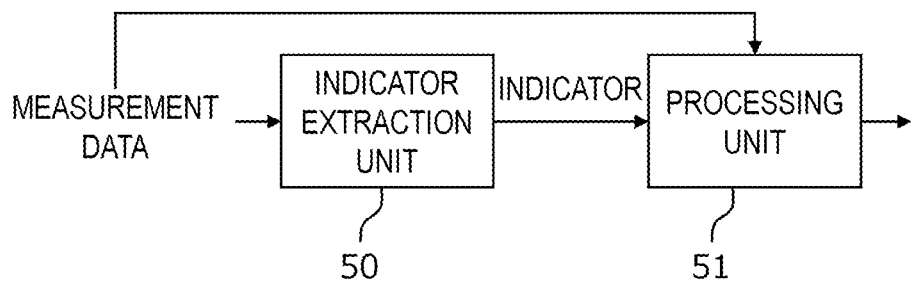
FIG. 5 is a block diagram illustrating processing that is performed by a biological information analysis device 1.

FIG. 5 is a block diagram illustrating processing that is performed by the biological information analysis device 1. As shown in FIG. 5, the biological information analysis device 1 includes an indicator extraction unit 50 and a processing unit 51. In the present embodiment, processing performed by the indicator extraction unit 50 and the processing unit 51 may be realized by the control unit 23 executing a program that is required for the processing. The program may be stored in the storage unit 27. When the control unit 23 executes the required program, the subject program stored in the ROM or storage unit 27 is loaded to the RAM. Then, the control unit 23 interprets and executes the program loaded to the RAM, using the CPU, to control each constituent component. Note that at least one or all of the processing procedures executed by the indicator extraction unit 50 and the processing unit 51 may be realized using a circuit such as an ASIC or an FPGA. Alternatively, at least one or all of the processing procedures executed by the indicator extraction unit 50 and the processing unit 51 may be realized using a computer (e.g. a smartphone, a tablet terminal, a personal computer, or a cloud server) that is separate from the main body 11.

The indicator extraction unit 50 acquires time-series data regarding blood pressure waveforms, which have been consecutively measured by the blood pressure measurement unit 20, from the storage unit 27. The indicator extraction unit 50 extracts, from the acquired time-series data regarding blood pressure waveforms, indicators that are related to characteristics of the blood pressure waveforms. Here, characteristics of a blood pressure waveform include, for example, characteristics of the shape of a blood pressure waveform corresponding to one heartbeat, temporal changes in a blood pressure waveform, and frequency components of a blood pressure waveform. However, characteristics of a blood pressure waveform are not limited to those listed above. The extracted indicators are output to the processing unit 51. There are various characteristics and indicators regarding a blood pressure waveform, and the characteristics and indicators that are to be extracted may be designed or selected as appropriate according to the purpose of processing that is to be performed by the processing unit 51. Characteristics and indicators that can be extracted from measurement data regarding blood pressure waveforms according to the present embodiment will be described later in detail.

When obtaining indicators, the indicator extraction unit 50 may use measurement data that has been acquired by the body movement measurement unit 21 and/or measurement data that has been acquired by the environment measurement unit 22, in addition to measurement data regarding blood pressure waveforms. Also, although not shown in the drawings, pieces of measurement data that have been acquired by a sleep sensor, a $SpO_2$ sensor, a respiration sensor (a flow sensor), a blood-sugar level sensor, and the like may be combined with one another. By performing complex analysis on a plurality of kinds of measurement data acquired by a plurality of sensors, it is possible to perform more advanced information analysis of a blood pressure waveform. For example, it is possible to classify pieces of data regarding blood pressure waveforms according to states of the user, such as a resting state and a moving state, a state when an atmospheric temperature is high and a state when it is low, a light sleep state and a deep sleep state, a breathing state and an apnea state, and so on. Alternatively, it is possible to extract information regarding the influence of body movement, an activity amount, activity intensity, a temperature change, apnea, the user's breathing, etc. on blood pressure, and thus evaluate the cause-effect relationship, the correlation, etc. between pieces of measurement data. Note that examples of apnea include obstructive sleep apnea, central sleep apnea, and mixed sleep apnea.

Figure 6:
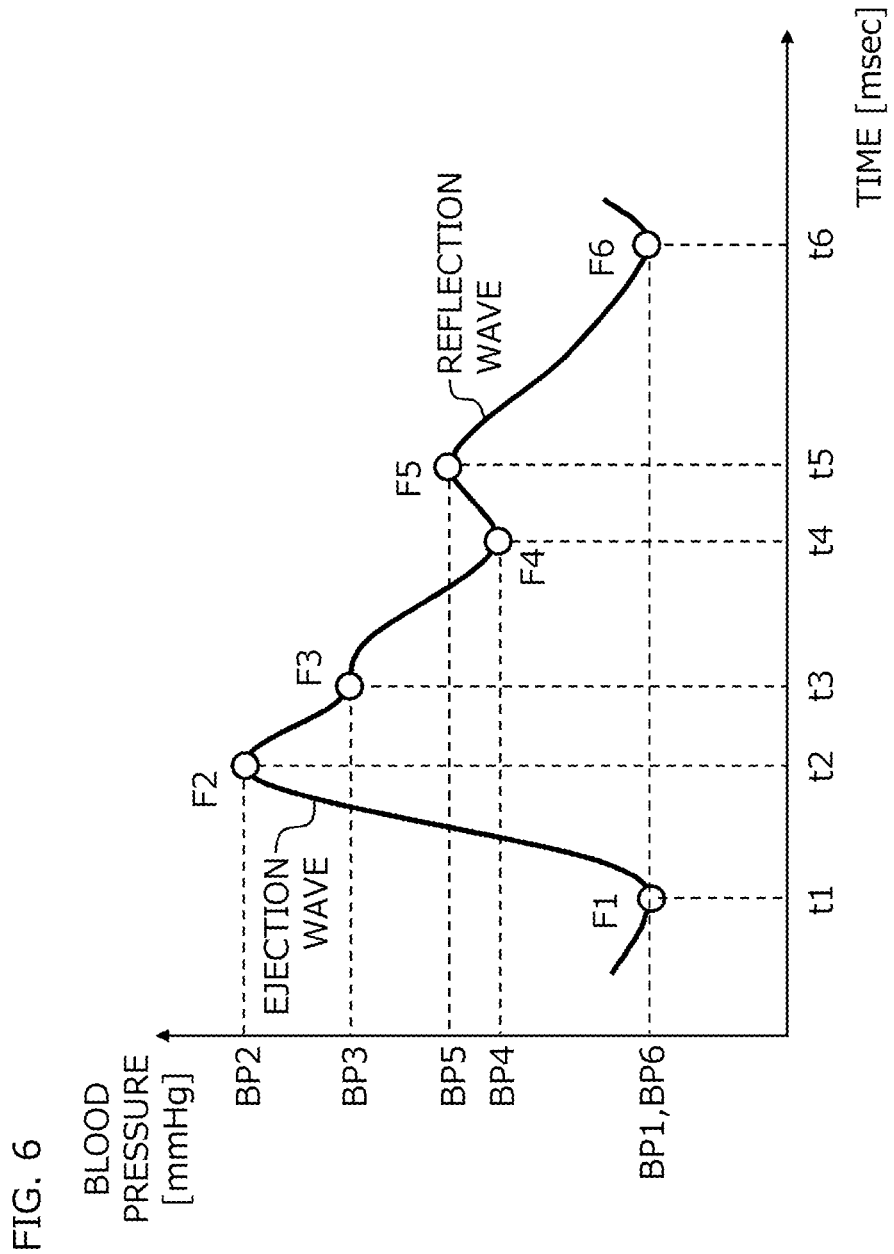
FIG. 6 shows a waveform (a blood pressure waveform) of a pressure pulse wave from a radial artery corresponding to one heartbeat.

The processing unit 51 receives the indicators extracted by the indicator extraction unit 50. The processing unit 51 performs processing that is based on the received indicators. Various kinds of processing can be conceived of as processing that is based on the indicators. For example, the processing unit 51 may provide the values of the extracted indicators or changes in the values to a user, a doctor, a public health nurse, or the like to prompt the utilization of the indicators in the fields of health care, treatment, health guidance, and so on. Alternatively, the processing unit 51 may estimate respiratory risks from the extracted indicators, or present guidelines for health maintenance or risk mitigation. Furthermore, when an increase in the risk of a cardiac disease occurring is detected or predicted based on an indicator, the processing unit 51 may inform the user or his/her doctor, or perform control to prevent the user from performing an action that places burden on his/her heart and so on, or to prevent a cardiovascular event from occurring.
Information Acquired from Blood Pressure Waveform FIG. 6 shows a waveform (a blood pressure waveform) of a pressure pulse wave from a radial artery corresponding to one heartbeat. The horizontal axis indicates time t (msec) and the vertical axis indicates blood pressure BP (mmHg).

A blood pressure waveform is the waveform of a composite wave constituted by an "ejection wave" that is generated when the heart contracts and pumps out blood, and a "reflection wave" that is generated when an ejection wave is reflected at a branch point of a peripheral vessel or an artery. The following shows examples of characteristic points that can be extracted from a blood pressure waveform corresponding to one heartbeat.

A point F1 is the rising point of the pressure pulse wave. The point F1 corresponds to the ejection start point of the heart, i.e. the point at which the aortic valve opens.

A point F2 is a point at which the amplitude (the pressure) of the ejection wave is at the maximum (a first peak).

A point F3 is an inflection point that appears midway in a drop in the ejection wave, due to a reflection wave being superimposed.

A point F4 is the minimum point, which appears between the ejection wave and the reflection wave, and is also referred to as a notch. This point corresponds to the point at which the aortic valve closes.

A point F5 is the peak of the reflection wave (a second peak), which appears after the point F4.

A point F6 is the end point of one heartbeat, and corresponds to the ejection start point of the next heartbeat, i.e. the start point of the next heartbeat.

The indicator extraction unit 50 may use any algorithm to detect the above-described characteristic points. For example, the indicator extraction unit 50 may perform computations to obtain an nth order differential waveform of a blood pressure waveform, and detect the zero-crossing points to extract the characteristic points (the inflection points) of the blood pressure waveform (the points F1, F2, F4, F5, and F6 can be detected from the first order differential waveform, and the point F3 can be detected from the second order differential waveform or the fourth order differential waveform). Alternatively, the indicator extraction unit 50 may read out, from the storage unit 27, a waveform pattern on which the characteristic points have been arranged in advance, and perform fitting of the waveform pattern to the target blood pressure waveform to specify the respective positions of the characteristic points.

The indicator extraction unit 50 performs computations based on time t and pressure BP of each of the above-described characteristic points F1 to F6, and can thus obtain various kinds of information (values, characteristic amounts, indicators, etc.) from the blood pressure waveform of one heartbeat. The following are typical examples of information that can be acquired from a blood pressure waveform. Note that tx and BPx respectively represent time and blood pressure corresponding to a characteristic point Fx.

Pulse Wave Interval (Period of Heartbeat) TA=t6−t1
Heart Rate PR=1/TA
Pulse Wave Rising Time UT=t2−t1
Systole TS=t4−t1
Diastole TD=t6−t4
Reflection Wave Delay Time=t3−t1
Maximum Blood Pressure (Systolic Blood Pressure) SBP=BP2
Minimum Blood Pressure (Diastolic Blood Pressure) DBP=BP1
Mean Blood Pressure MAP=(Area of Blood Pressure Waveform from t1 to t6)/Period of Heartbeat TA
Mean Blood Pressure during Systole=(Area of Blood Pressure Waveform from t1 to t4)/Systole TS
Mean Blood Pressure during Diastole=(Area of Blood Pressure Waveform from t4 to t6)/Diastole TD
Pulse Pressure PP=Maximum Blood Pressure SBP−Minimum Blood Pressure DBP
Late Systolic Pressure SBP2=BP3
AI (Augmentation Index)=(Late Systolic Pressure SBP2−Minimum Blood Pressure DBP)/Pulse Pressure PP Basic statistics of these pieces of information (values, characteristic amounts, and indicators) can also be used as indicators. Basic statistics include, for example, representative values (a mean value, a median value, a mode value, the maximum value, the minimum value, and so on) and the degree of scatter (dispersion, a standard deviation, a coefficient of variation, and so on). Temporal changes in these pieces of information (values, characteristic values, and indicators) can also be used as indicators.

In addition, the indicator extraction unit 50 can also acquire an indicator called BRS (Baroreflex Sensitivity) by performing computations on pieces of heartbeat information. This indicator indicates the ability to regulate blood pressure to be constant. Examples of methods for calculating the indicator include a spontaneous sequence method. This is a method for only extracting a sequence in which the maximum blood pressure SBP and the pulse wave interval TA consecutively rise or fall over the period of three or more heartbeats in synchronization with each other, plotting the maximum blood pressure SBP and the pulse wave interval TA onto a two-dimensional plane, and defining the inclination of the regression line obtained through a least squares method as the BRS.

The following illustrates several examples, which are specific applications, of the biological information analysis system 10.

EXAMPLE 1

The present example is an example in which a cardiac state and the risk of a cardiac disease occurring are represented as indicators based on instantaneous stroke volumes corresponding to blood pressure waveforms that are consecutively measured.

A stroke volume (SV, which is also referred to as "cardiac output") is known as an evaluation indicator that indicates a cardiac state and the risk of cardiac hypertrophy or cardiac expansion occurring. The stroke volume (SV) also indicates cardiac preload. The stroke volume (SV) can be calculated as follows, using a pulse pressure (PP) and an aortic stiffness (denoted as Stiffness, which is the inverse of compliance C): SV=PP/Stiffness. Here, provided that a period in which aortic stiffness (Stiffness) does not change is used, the stroke volume may be represented as follows: SV=PP.

Also, the stroke volume (SV) can also be calculated as follows, based on blood pressure waveform data acquired by using a tonometry method: $SV=\Delta P+P_{AV} \times T$. Here, $\Delta P$ denotes the difference between the value of blood pressure at the end of ejection and the value of blood pressure at the start of ejection, $P_{AV}$ denotes the mean value of blood pressure during ejection, and T denotes the duration of ejection. This calculation formula shows better correlation with the stroke volume.

Although it is possible to use the stroke volume to evaluate the risk of cardiac expansion or cardiac hypertrophy occurring, conventional blood pressure measurement devices have issues, i.e. the stroke volume cannot be measured for each heartbeat (spot blood pressure meters), accuracy is not satisfactory (pulse oximeters), and ambulatory blood pressure cannot be measured for a long period of time (e.g. overnight) (conventional devices using an invasive method or a tonometry method). Therefore, the present example proposes a method for easily ascertaining the cardiac state and the risk of a cardiac disease occurring, by using the stroke volume of every single beat measured over a long period of time.

Indicators

In the present example, blood pressure waveform data is measured over a long period of time (e.g. overnight, or over several days), and the SV value of every single beat is obtained, and indicators that represent a cardiac state (cardiac state indicators) are obtained based on the distribution of SV values. The cardiac state indicators can be regarded as indicators that indicate the risk of a cardiac disease occurring.

The SV value per heartbeat is an indicator that represents instantaneous cardiac load, and is an example of an instantaneous cardiac load indicator. In the following description, the SV value per heartbeat is also referred to as an instantaneous SV value (an instantaneous stroke volume). In the present example, cardiac state indicators are calculated based on the distribution of instantaneous SV values.

Figure 7A:
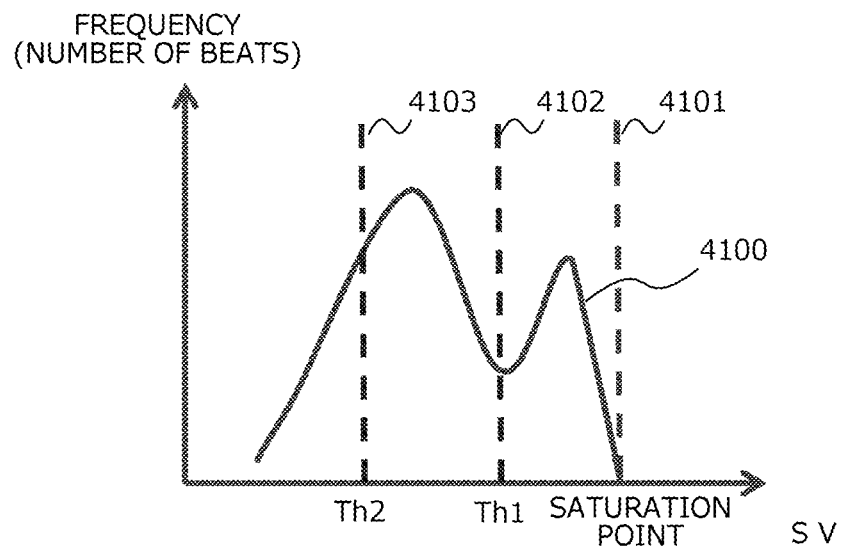
FIG. 7A is a graph showing distribution of SV values according to Example 1.

FIG. 7(A) is a graph 4100 showing the distribution of instantaneous SV values measured in a measurement period. A dotted line 4101 in the figure represents the maximum value (saturation point) of the SV value of a user that is the subject of measurement. It is preferable that the SV value at the saturation point has been determined in advance by performing measurement under an exercise load. Alternatively, if the user performs exercise at more than a predetermined intensity in the measurement period, the maximum value of the SV value in the period may be employed as the saturation point. Exercise at a predetermined intensity is exercise at an intensity that saturates the SV value of a user that is the subject of measurement.

A first cardiac state indicator INDEX1 in the present example indicates the proportion of the frequency of SV values that are higher than a threshold value Th1. That is, the indicator INDEX1 indicates the proportion of the frequency of the SV values between the dotted line 4101 and a dotted line 4102, relative to the overall frequency. Here, the threshold value Th1 can be determined based on the SV value at the saturation point, and can be 80% of the SV value at the saturation point, for example. It can be said that the indicator INDEX1 indicates the proportion of the frequency of excessive preload. Therefore, it is possible to ascertain the risk of cardiac expansion occurring, based on the magnitude of the indicator INDEX1. Note that the threshold value Th1 is not necessarily 80% of the SV value at the saturation point, and may be a value within the range of 70% to 90% of the SV value at the saturation point, or another value.

A second cardiac state indicator INDEX2 in the present example indicates the proportion of the frequency of SV values that are lower than a threshold value Th2. That is, the indicator INDEX2 indicates the proportion of the frequency of the SV values that are no greater than the value indicated by a dotted line 4103, relative to the overall frequency. Here, the threshold value Th2 is determined based on the lower limit of a typical reference value, and may be the same value for every user. For example, the threshold value Th2 may be a value that is based on 60 ml/beat. It can be said that the indicator INDEX2 indicates the proportion of the frequency of a drop in preload. Therefore, it is possible to ascertain the risk of a blood clot being formed, based on the magnitude of the indicator INDEX2.

A third indicator INDEX3 in the present example indicates the SV value at the saturation point (the maximum instantaneous stroke volume). As described above, it is preferable that the saturation point SV value has been measured in advance by performing measurement under an exercise load. However, the saturation point SV value may be measured while the user is performing exercise during a measurement period, at an intensity that is no less than a predetermined intensity, and determined as the maximum value of the instantaneous SV value. The stroke volume SV is saturated when the expansion of the myocardial fibers exceeds the limit. If the saturation point SV value is small, it can be determined that the limit of expansion of the cardiac muscle has decreased and the capacity of the heart has decreased. That is, it is possible to ascertain the risk of cardiac hypertrophy occurring, based on the saturation point SV value. It is also possible to determine that the risk of cardiac hypertrophy occurring is high if the saturation point SV value is no greater than a threshold value $SV_{Th}$. The threshold value $SV_{Th}$ can be determined based on the lower limit of a typical reference value. For example, the threshold value $SV_{Th}$ may be a value that is based on 60 ml/beat.

Examples of Screen Display

In the present example, it is preferable that a histogram of SV values as shown in FIG. 7(A) or the above-described indicators INDEX1 to INDEX3 that can be obtained from the histogram are displayed through screen display.

Figure 7B:
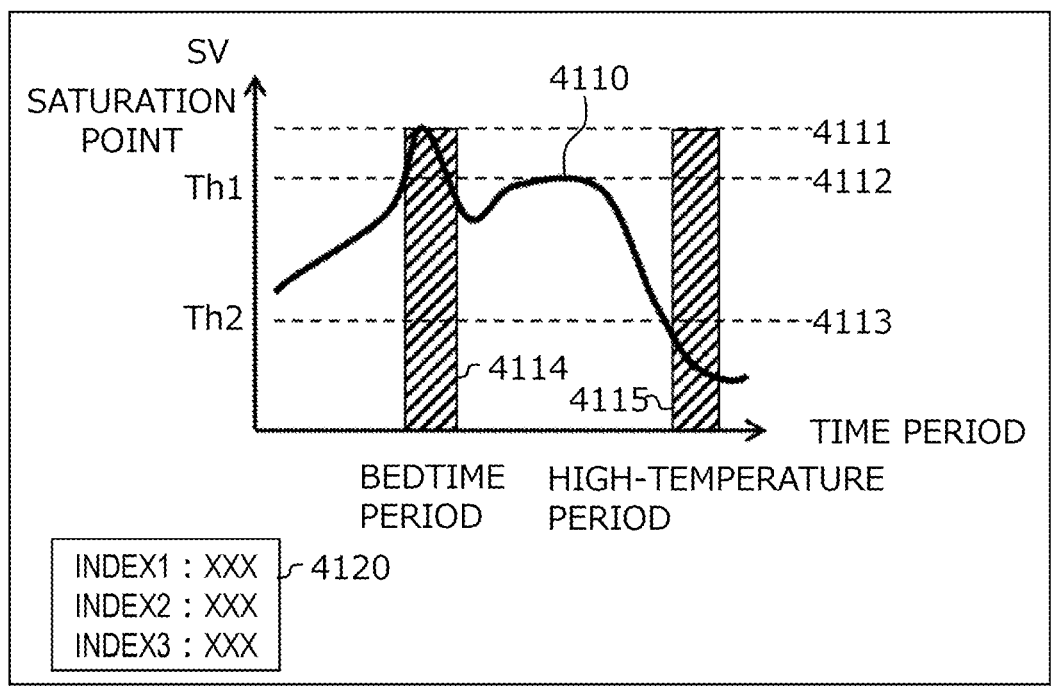
FIG. 7B is a graph showing temporal changes.

It is also preferable that the above-described indicators INDEX1 to INDEX3 are displayed together with a graph showing temporal changes in the SV value as shown in FIG. 7(B). A graph 4110 shows temporal changes in the SV value, a dotted line 4111 shows the maximum value of the SV value, a dotted line 4112 shows the threshold value Th1, and a dotted line 4113 shows the threshold value Th2. A display 4120 shows the values of the cardiac state indicators INDEX1 to INDEX3. If it has been determined that the risk of a cardiac disease occurring is high, the values of the indicators INDEX1 to INDEX3 may be displayed in a different display mode with a different color or size so as to be emphasized, or displayed with a message indicating that the risk is high. Alternatively, the values of the indicators INDEX1 to INDEX3 may be displayed only when it has been determined that the risk is high. Such graph display makes it easier to ascertain the cardiac state of the user and the risk of a cardiac disease occurring, and also makes it easier to ascertain when a change in the stroke volume that may cause a cardiac disease has occurred.

It is also preferable that the instantaneous SV value is displayed in association with the state of the user and the state of the environment. For example, as shown in FIG. 7(B), it is preferable that a graph showing temporal changes in the SV value is displayed in a mode in which a bedtime period 4114 and a high-temperature period 4115 are discernible. This makes it possible to determine a probable cause of a change in the SV value. For example, it is possible to determine that a cause of an increase in the SV value during the bedtime period is a respiratory abnormality, and a cause of a decrease in the SV value during the high-temperature period is dehydration. Thus, the graph is useful for prevention and treatment. Note that a sleeping state can be identified based on measurement data or measurement time data acquired by the body movement measurement unit 21. Temperature information such as that indicating a high temperature can be identified based on measurement data acquired by the environment measurement unit 22. These pieces of information may be acquired based on information that has been input by the user or a third party (such as a doctor) to the input unit 24.

In another example in which the instantaneous SV value and the state of the environment are displayed in association with each other, it is also preferable that temporal changes in an influencing factor (such as an atmospheric temperature) and another indicator are superimposed and displayed on the above-described graph 4110. Superimposed display of an influencing factor and temporal changes in the SV value is useful for identification of the cause of an increase in the SV value.

Figure 7C:
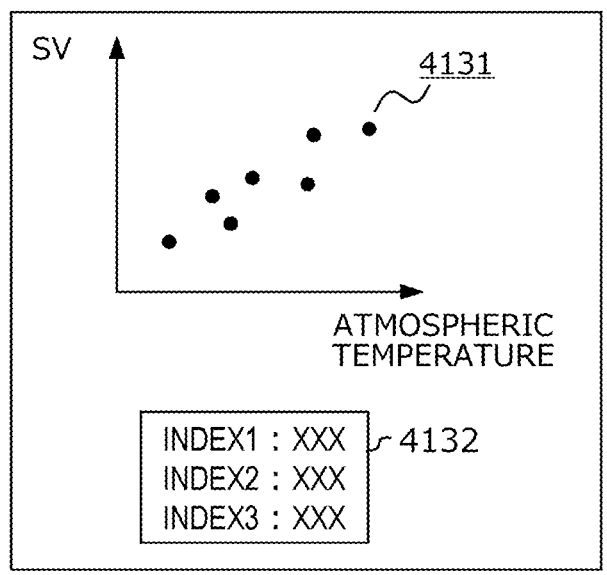
FIG. 7C is a scatter diagram.

In yet another example in which the instantaneous SV value and the state of the environment are displayed in association with each other, measurement data displayed in the form of a scatter diagram that is defined by an axis indicating the SV value and an axis indicating the influencing factor, as shown in FIG. 7(C), is also useful. For example, a scatter diagram in which each of the plotted points has an SV value and a measurement value of the influencing factor corresponding to the same point in time as the x coordinate value and the y coordinate value, respectively, may be used. Such display is useful when determining whether or not the influencing factor thus displayed is a cause of a cardiac load. Therefore, by displaying a plurality of influencing factors as in FIG. 7(C), it is possible to identify the cause of a cardiac load.

Example of Processing

FIG. 8 is a flowchart for processing according to the present example. In step S101, the user's data regarding consecutive blood pressure waveforms is measured. That is, the user goes about his/her life as usual wearing the biological information analysis system 10. During the measurement period, the blood pressure measurement unit 20 measures blood pressure waveforms, and store the measurement data in the local storage unit 27 or in a memory in a cloud server by transmitting the measurement data using the communication unit 26. At the same time, the body movement measurement unit 21 and the environment measurement unit 22 stores data acquired from sensors in a memory in a similar manner. The length of the measurement period in step S101 is not specifically limited, and may be one night, several days, or longer.

The output unit 25 may output, to the user, an instruction to perform exercise at least once in the measurement period, at an intensity that is no less than a predetermined intensity.

Upon completion of the measurement in step S101, the indicator extraction unit 50 calculates an SV value for each heartbeat, as an instantaneous cardiac load indicator. Specifically, the indicator extraction unit 50 first acquires measurement data regarding the measured blood pressure waveforms from the storage unit 27 or a cloud server, and divides the data into pieces that each correspond to one beat. This division can be realized by calculating ejection start points (the point F1 in FIG. 6) from the blood pressure waveform data, and determining data between two ejection start points that are adjacent to each other as data corresponding to one beat. Then, the indicator extraction unit 50 calculates an SV value for each beat. Here, although SV=PP may be employed, $SV=\Delta P+P_{AV}\times T$ is preferable.

In step S103, the indicator extraction unit 50 calculates a cardiac state indicator based on the distribution of SV values that each correspond to one heartbeat. More specifically, the indicator extraction unit 50 calculates, as the indicator INDEX1, the proportion of the number of beats that correspond to an SV value that is no less than the threshold value Th1, relative to the total number of beats. Also, the indicator extraction unit 50 calculates, as the indicator INDEX2, the proportion of the number of beats that correspond to an SV value that is less than the threshold value Th2, relative to the total number of beats. Also, the indicator extraction unit 50 calculates, as the indicator INDEX3, the maximum value of the instantaneous SV value, i.e. the saturation point SV value, in the measurement data. Note that the INDEX1 and the INDEX2 are not necessarily the above-described proportions themselves, and may be values determined based on the proportions. Similarly, the INDEX3 is not necessarily the saturation SV value, and may be a value determined based on the saturation SV value.

In step S104, the processing unit 51 outputs an image display that includes the cardiac state indicators INDEX1 to INDEX3 calculated in step S103.

For example, as shown in FIG. 7(B), the processing unit 51 generates image data that includes the display 4120 that indicates the numerical values of the cardiac state indicators INDEX1 to INDEX3, and the graph 4110 that indicates temporal changes in the instantaneous SV value during the measurement period, and outputs the image data using the output unit 25. The horizontal axis and the vertical axis of the graph 4110 respectively indicate time and the SV value (the cardiac load indicator). The graph is displayed in a mode in which the threshold values Th1 and Th2 are discernible. Therefore, the user or a doctor or the like can easily ascertain a period of time in which cardiac load increases or decreases.

Furthermore, the processing unit 51 may specify a period of time in which the user is in a specific state, based on the measurement data (and periods of time) acquired by the body movement measurement unit 21, and display a graph in a mode in which the period of time is discernible. For example, the period 4114 is a period of time in which the user's body moves less frequently, and is a night-time period. Therefore, the processing unit 51 may specify the period 4114 as a bedtime period. Also, the processing unit 51 may specify a period of time in which the user is in a moving state, based on a large amount of body movement of the user, or specify, as a wake-up time, a point in time at which the user's body movement starts increasing from that in the sleeping state. Also, the processing unit 51 may specify a period of time in which the environment is in a specific state, based on the measurement data acquired by the environment measurement unit 22, and, for example, display a graph in a mode in which the period of time is discernible. For example, the processing unit 51 may acquire an environmental temperature, and specify, as a high-temperature state period, a period of time in which the environmental temperature is no less than a threshold value. By displaying a user state or an environmental state together, it is possible to allow the user or a doctor to easily understand what is the cause of an increase or a decrease in cardiac load.

Although the cardiac state indicators INDEX1 to INDEX3 in the example in FIG. 7(B) are displayed as numerical values, the processing unit 51 may display the cardiac state indicators INDEX1 to INDEX3 in a mode other than numerical values. Also, the processing unit 51 may display, for example, a message indicating that the risk of cardiac expansion occurring is high if the indicator INDEX1 is no less than a threshold value, a message indicating that the risk of a blood clot being formed if the indicator INDEX2 is no greater than a threshold value, and a message indicating that the risk of cardiac hypertrophy occurring is high if the indicator INDEX3 is no greater than a threshold value.

FIG. 7(C) is an example of an output screen that includes a scatter diagram 4131 showing a relationship between an influencing factor (the temperature in this example) and the SV value, and a display 4132 showing the cardiac state indicators INDEX1 to INDEX3. The processing unit 51 acquires an SV value and measurement data regarding the temperature corresponding to the same point in time, from the storage unit 27 (or a cloud server), and generates image data for a scatter diagram 4131 that includes a plurality of points each having a temperature value and an SV value as the x coordinate value and the y coordinate value, respectively. The cardiac state indicators INDEX1 to INDEX3 are the same as those in FIG. 7(B), and therefore descriptions thereof are omitted.

According to the present example, it is possible to make it easier to ascertain the cardiac state and the risk of a cardiac disease occurring, and also identify a cause that increase the risk of a cardiac disease occurring, using the SV value of every single beat measured during a long period of time. In particular, since blood pressure waveform data of each beat is available, it is possible to ascertain an instantaneous cardiac load at the time a sharp change occurs in blood pressure.

EXAMPLE 2

The present example is an example in which the risk of a cardiac disease occurring is represented as an indicator.

Total peripheral resistance (TPR) is known as an evaluation indicator indicating a cardiac state and the risk of cardiac hypertrophy occurring. The total peripheral resistance (TPR) is also an indicator that indicates cardiac afterload.

The total peripheral resistance (TPR) can be calculated as follows, based on blood pressure waveform data acquired by using a tonometry method: TPR=MBP·Stiffness/(PP·PR). Here, MBP denotes a mean blood pressure, PP denotes a pulse pressure, PR denotes a pulse rate, and Stiffness denotes an aortic stiffness (the inverse of compliance C).

With respect to a period of time that is not so long that the aortic stiffness (Stiffness) does not change in the period, the total peripheral resistance may be represented as follows: TPR=MBP/(PP·PR).

Although it is possible to use the total peripheral resistance to evaluate the risk of cardiac hypertrophy occurring, conventional blood pressure measurement devices have problems, i.e. the total peripheral resistance cannot be measured for each beat (spot blood pressure meters), accuracy is unsatisfactory (pulse oximeters), and ambulatory blood pressure cannot be measured for a long period of time (e.g. overnight) (conventional devices using an invasive method or a tonometry method). Therefore, the present example proposes a method for easily ascertaining a cardiac state and the risk of a cardiac disease occurring, by using the total peripheral resistance of every single beat measured over a long period of time.

Indicators

In the present example, blood pressure waveform data is measured over a long period of time (e.g. overnight, or over several days), and the TPR value of every single beat is obtained, and indicators that represent a cardiac state (cardiac state indicators) are obtained based on the distribution of TPR values. The cardiac state indicators can be regarded as indicators that indicate the risk of a cardiac disease occurring.

The TPR value per heartbeat is an indicator that represents instantaneous cardiac load, and is an example of an instantaneous cardiac load indicator. In the following description, the TPR value per heartbeat is also referred to as an instantaneous TPR value (an instantaneous total peripheral resistance). In the present example, cardiac state indicators are calculated based on the distribution of instantaneous TPR values.

Figure 9A:
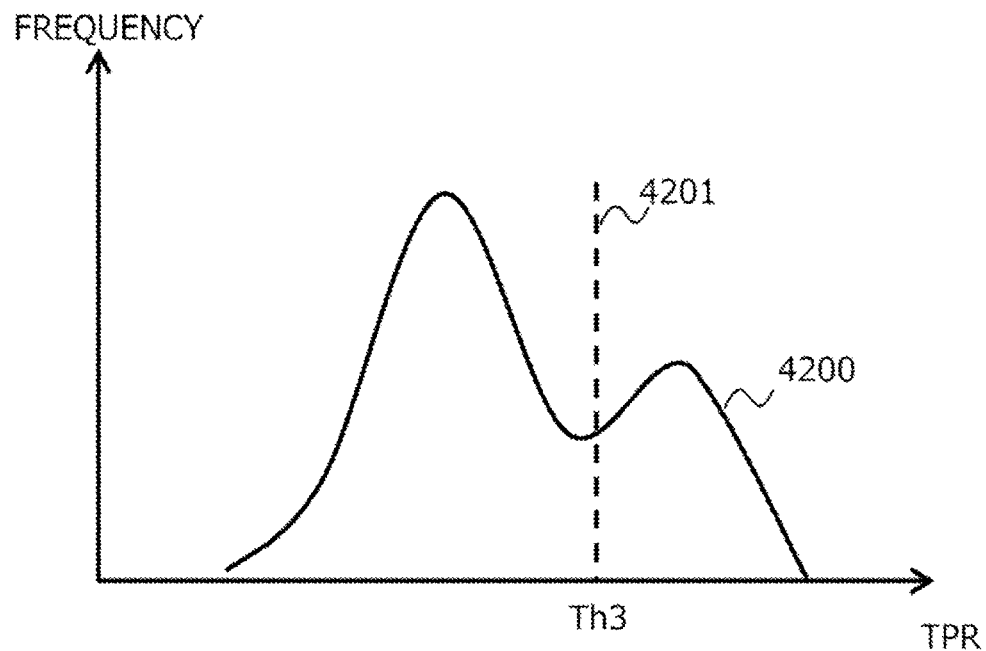
FIG. 9A is a graph showing distribution of TPR values according to Example 2.

FIG. 9(A) is a graph 4200 showing the distribution of instantaneous TPR values measured in a measurement period. A cardiac state indicator INDEX4 in the present example indicates the proportion of the frequency of TPR values that are no less than a threshold value Th3. That is, the indicator INDEX4 indicates the proportion of the frequency of the TPR values that are no less than the value indicated by a dotted line 4201, relative to the overall frequency. Here, if a value is no less than the threshold value Th3, it is determined that excessive afterload has occurred. The threshold value Th3 can be determined based on the upper limit of a typical reference value. For example, the threshold value Th3 may be 1200 dynes·sec/cm$^5$.

A TPR value no less than the threshold value Th3 indicates that excessive afterload has occurred. Therefore, it can be said that the indicator INDEX4 indicates the proportion of the frequency of excessive afterload. Therefore, it is possible to ascertain the risk of cardiac hypertrophy occurring, based on the magnitude of the indicator INDEX4.

Examples of Screen Display

In the present example, it is preferable that a histogram of TPR values as shown in FIG. 9(A) or the above-described indicator INDEX4 that can be obtained from the histogram is displayed through screen display.

Figure 9B:
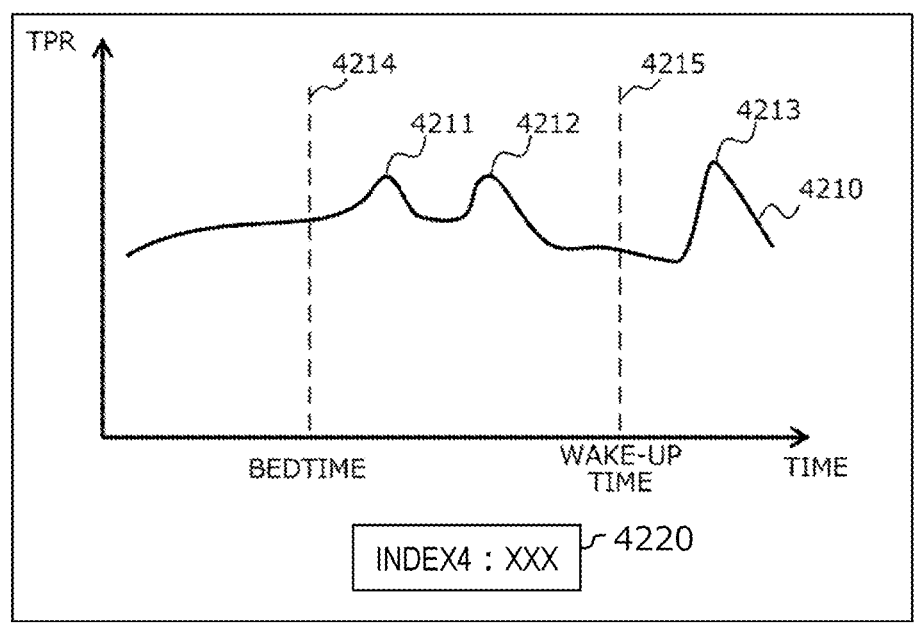
FIG. 9B is a graph showing temporal changes.

It is also preferable that the above-described indicator INDEX4 is displayed together with a graph showing temporal changes in the TPR value as shown in FIG. 9(B). A graph 4210 shows temporal changes in the TPR value. A display 4220 shows the value of the cardiac state indicator INDEX4. If it has been determined that the risk of a cardiac disease occurring is high, the value of the indicator INDEX4 may be displayed in a different display mode with a different color or size so as to be emphasized, or displayed with a message indicating that the risk is high. Alternatively, the value of the indicator INDEX 4 may be displayed only when it has been determined that the risk is high. Such graph display makes it easier to ascertain the cardiac state of the user and the risk of a cardiac disease occurring, and also makes it easier to ascertain when a change in the TPR value that may cause a cardiac disease has occurred.

It is also preferable that a graph is displayed in a mode in which a bedtime 4214 and a wake-up time 4215 are discernible as shown in FIG. 9(B). In addition, it is also preferable that a meal period, an exercise period, and on are displayed.

By displaying the TPR value and the wake-up time, the bedtime, and so on together, it is possible to make it easier to identify the cause of an increase in the TPR value. For example, increases in the TPR value at a point 4211 and a point 4212 occurred in a night-time period, and therefore it can be envisaged that these increases were caused by sleep apnea. Therefore, a comparison with another apnea indicator makes it possible to identify the cause. Also, an increase in the TPR value at a point 4213 after the wake-up time (in the morning) is likely to be an increase caused by a rise in the atmospheric temperature. Therefore, a comparison with the atmospheric temperature makes it possible to identify the cause.

It is also preferable to superimpose and display temporal changes in another indicator (e.g. an indicator indicating a sleep apnea) or an influencing factor (e.g. an atmospheric temperature) on the above-described graph. Superimposed display of temporal changes in the TPR value is useful for identification of the cause of an increase in the TPR value.

Furthermore, it is also preferable to display measurement data in the form of a scatter diagram that is defined by an axis indicating the TPR value and an axis indicating the influencing factor. Such display is useful for identification of the cause of cardiac load.

Note that influencing factors such as the wake-up time, the bedtime, and the atmospheric temperature can be acquired from the body movement measurement unit 21 and the environment measurement unit 22, or acquired based on an input from the user to the input unit 24.

Example of Processing

Processing in the present example is performed according to the flowchart shown in FIG. 8, as in Example 1. The following mainly describes differences from Example 1.

The processing in step S101 is the same as that in Example 1. Step S102 is the same as that in Example 1 in that a blood pressure waveform is divided into pieces of data that each correspond to one beat. However, an instantaneous cardiac load indicator that is calculated from a piece of data corresponding to one beat is different from that in Example 1. In the present example, the indicator extraction unit 50 calculates a TPR value for each heartbeat, as an instantaneous cardiac load indicator. Here, the indicator extraction unit 50 calculates a TPR value as follows: TPR=MBP/(PP·PR).

In step S103, the indicator extraction unit 50 calculates, as the indicator INDEX4, the proportion of the number of beats that correspond to a TPR value that is no less than the threshold value Th3, relative to the total number of beats.

In step S104, the processing unit 51 outputs a screen display as shown in FIG. 9(B). At this time, if the indicator INDEX4 is no less than the threshold value, the processing unit 51 displays a message indicating that there is a risk of cardiac hypertrophy occurring. In FIG. 9(B), the processing unit 51 generates a display screen in a mode in which points in time at which the user performed particular operations (such as the bedtime and the wake-up time) are discernible. However, the processing unit 51 may generate a display screen in a mode in which points in time at which the user or the environment is in a particular state are discernible as in Example 1.

According to the present example, it is possible to make it easier to ascertain the risk of a cardiac disease occurring, and also identify a cause that increases the risk of a cardiac disease occurring, using the TPR value of every single beat measured during a long period of time. In particular, since blood pressure waveform data of each beat is available, it is possible to ascertain instantaneous cardiac load at the time a sharp change occurs in blood pressure.

Modifications

An increase in the instantaneous TPR value may be caused by apnea. Therefore, an increase in the instantaneous TPR value that occurs while the user is sleeping can be used as a sign indicating a risk of a respiratory abnormality (a cardiovascular disease) such as sleep apnea occurring. Thus, upon detecting that the instantaneous TPR value has increased to be no less than the threshold value Th3 while the user is sleeping, the processing unit 51 may output a message indicating that there is the risk of a respiratory abnormality occurring, from the output unit 25. Sleep can be detected based on measurement data and measurement time acquired by the body movement measurement unit 21, for example.

Also, an increase in the instantaneous TPR value may be caused by the atmospheric temperature. For example, if the instantaneous TPR value has increased in the morning, the cause of the increase may be a rise in the atmospheric temperature. Therefore, it is possible to determine whether or not the cause of an increase in the instantaneous TPR value is a rise in the atmospheric temperature by referring to measurement data of the atmospheric temperature at the time the instantaneous TPR value has increased. That is, it is possible to ascertain the atmospheric-temperature sensitivity of the user's blood pressure by examining the correlation between an increase in the instantaneous TPR value and the atmospheric temperature. For example, upon detecting that the user's instantaneous TPR value has increased to be no less than the threshold value Th3 in a morning-time period, the processing unit 51 may output, from the output unit 25, a message indicating that the atmospheric-temperature sensitivity of the user's blood pressure is high. Alternatively, if temperature data acquired during a blood pressure measurement period is available, the processing unit 51 may acquire temperature data during a period in which the instantaneous TPR has increased, and determine whether or not the atmospheric temperature has increased in the period. If it is determined that the atmospheric temperature has increased in the period, the processing unit 51 may specify the atmospheric temperature as the cause of the increase in the instantaneous TPR value in the morning-time period, and output a message indicating that, from the output unit 25.

SUPPLEMENTARY NOTE 1

A biological information analysis device comprising:
a hardware processor; and a memory that is configured to store a program,
wherein the hardware processor is configured to execute the program to
acquire data regarding blood pressure waveforms that are consecutively measured by a sensor that is configured to be worn on a body part of a user and to be capable of non-invasively measuring a blood pressure waveform for each heartbeat,
extract a value of a cardiac load indicator for each heartbeat, from the data regarding blood pressure waveforms,
calculate an indicator indicating a cardiac state, based on characteristics related to distribution of values of the cardiac load indicator corresponding to a plurality of heartbeats, and
output the indicator indicating the cardiac state.

SUPPLEMENTARY NOTE 2

A biological information analysis system comprising:
a sensor that is configured to be worn on a body part of a user and to be capable of non-invasively measuring a blood pressure waveform for each heartbeat; a hardware processor; and a memory that is configured to store a program,
wherein the hardware processor is configured to execute the program to
acquire data regarding blood pressure waveforms that are consecutively measured by the sensor, extract a value of a cardiac load indicator for each heartbeat, from the data regarding blood pressure waveforms, calculate an indicator indicating a cardiac state, based on characteristics related to distribution of values of the cardiac load indicator corresponding to a plurality of heartbeats, and output the indicator indicating the cardiac state.

SUPPLEMENTARY NOTE 3

A biological information analysis method comprising:

a step of acquiring data regarding blood pressure waveforms that are consecutively measured by a sensor that is configured to be worn on a body part of a user and to be capable of non-invasively measuring a blood pressure waveform for each heartbeat, using at least one hardware processor;

a step of extracting a value of a cardiac load indicator for each heartbeat, from the data regarding blood pressure waveforms, using at least one hardware processor;

a step of calculating an indicator indicating a cardiac state, based on characteristics related to distribution of values of the cardiac load indicator corresponding to a plurality of heartbeats, using at least one hardware processor; and a step of outputting the indicator indicating the cardiac state, using at least one hardware processor.

INDEX TO THE REFERENCE NUMERALS

1 . . . biological information analysis device, 2 . . . measurement unit

10 . . . biological information analysis system, 11 . . . main body, 12 . . . belt 20 . . . blood pressure measurement unit, 21 . . . body movement measurement unit, 22 . . . environment measurement unit, 23 . . . control unit, 24 . . . input unit, 25 . . . output unit, 26 . . . communication unit, 27 . . . storage unit 30 . . . pressure sensor, 31 . . . pressurizing mechanism, 300 . . . pressure detection element 50 . . . indicator extraction unit, 51 . . . processing unit

The invention claimed is:

1. A biological information analysis device comprising at least one memory and at least one processor which function as:

an indicator extraction unit configured to extract an indicator indicating a cardiac state, from data regarding blood pressure waveforms that are consecutively measured by a sensor that is configured to be wearable on a body part of a user and capable of non-invasively measuring a blood pressure waveform for each heartbeat; and a processing unit configured to output the indicator extracted by the indicator extraction unit, wherein the indicator extraction unit is configured to extract a value of a cardiac load indicator for each heartbeat, from the data regarding blood pressure waveforms, wherein the indicator indicating the cardiac state is determined based on at least one of:

a frequency with which a stroke volume exceeds a first threshold value in a distribution of the value of the cardiac load indicator determined based on a stroke volume for each heartbeat wherein a state in which an instantaneous stroke volume is greater than the first threshold value is a state in which excessive preload has occurred, and the first threshold value is determined based on the maximum value of the instantaneous stroke volume of the user, a frequency with which the stroke volume falls below a second threshold value in the distribution of the value of the cardiac load indicator determined based on the stroke volume for each heartbeat wherein a state in which the instantaneous stroke volume is smaller than the second threshold value is a state in which preload is excessively low, and the second threshold value is determined based on the lower limit of a typical reference value of the stroke volume, and a frequency with which a total peripheral resistance exceeds a third threshold value in the distribution of the value of the cardiac load indicator determined based on the total peripheral resistance for each heartbeat wherein a state in which an instantaneous total peripheral resistance is greater than the third threshold value is a state in which excessive afterload has occurred, and the third threshold value is determined based on the upper limit of a typical reference value of the total peripheral resistance.

2. The biological information analysis device according to claim 1, wherein the indicator indicating the cardiac state is determined based on the maximum value of the stroke volume in the distribution.

3. The biological information analysis device according to claim 1, wherein the processing unit is configured to output temporal changes in values of the cardiac load indicator corresponding to a plurality of heartbeats, and the indicator indicating the cardiac state.

4. The biological information analysis device according to claim 3, wherein the processing unit is configured to acquire, from a second sensor, data indicating at least one of the user's body movement and the state of the environment during measurement of blood pressure waveforms, and output temporal changes in the cardiac load indicator in association with at least one of the user's body movement and the state of the environment.

5. The biological information analysis device according to claim 3, wherein the processing unit is configured to acquire, from a second sensor, time-series data indicating the state of the environment during measurement of blood pressure waveforms, and output the cardiac load indicator and the state of the environment in association with each other.

6. A system comprising:

a sensor that is configured to be worn on a body part of a user and capable of non-invasively measuring a blood pressure waveform for each heartbeat; and the biological information analysis device according to claim 1, the biological information analysis device being configured to analyze biological information, using data regarding blood pressure waveforms consecutively measured by the sensor.

7. A non-transitory computer-readable medium storing a program that causes a processor to function as the indicator extraction unit and the processing unit of the biological information analysis device according to claim 1.

8. A biological information analysis method comprising:

a step of acquiring, by at least one processor, data regarding blood pressure waveforms that are consecutively measured by a sensor that is configured to be wearable on a body part of a user and capable of non-invasively measuring a blood pressure waveform for each heartbeat;

a step of extracting, by the at least one processor, a value of a cardiac load indicator for each heartbeat, from the data regarding blood pressure waveforms; and a step of outputting, by the at least one processor, an indicator indicating a cardiac state, wherein the indicator indicating the cardiac state is determined based on at least one of:

a frequency with which a stroke volume exceeds a first threshold value in a distribution of the value of the cardiac load indicator determined based on the stroke volume for each heartbeat wherein a state in which an instantaneous stroke volume is greater than the first threshold value is a state in which excessive preload has occurred, and the first threshold value is determined based on the maximum value of the instantaneous stroke volume of the user, a frequency with which the stroke volume falls below a second threshold value in the distribution of the value of the cardiac load indicator determined based on the stroke volume for each heartbeat wherein a state in which the instantaneous stroke volume is smaller than the second threshold value is a state in which preload is excessively low, and the second threshold value is determined based on the lower limit of a typical reference value of the stroke volume, and a frequency with which a total peripheral resistance exceeds a third threshold value in the distribution of the value of the cardiac load indicator determined based on the total peripheral resistance for each heartbeat wherein a state in which an instantaneous total peripheral resistance is greater than the third threshold value is a state in which excessive afterload has occurred, and the third threshold value is determined based on the upper limit of a typical reference value of the total peripheral resistance.

* * * * *